(12) United States Patent
Roffler et al.

(10) Patent No.: US 7,320,791 B2
(45) Date of Patent: Jan. 22, 2008

(54) MONOCLONAL ANTIBODY FOR ANALYSIS AND CLEARANCE OF POLYETHYLENE GLYCOL AND POLYETHYLENE GLYCOL-MODIFIED MOLECULES

(75) Inventors: Steve Roffler, Taipei (TW); Tian-Lu Cheng, Chang Hua (TW); Pin-Yi Wu, Taipei (TW)

(73) Assignee: Academia Sinica, Taipei (TW)

( * ) Notice: Subject to any disclaimer, the term of this patent is extended or adjusted under 35 U.S.C. 154(b) by 253 days.

(21) Appl. No.: 10/620,091

(22) Filed: Jul. 15, 2003

(65) Prior Publication Data

US 2004/0014156 A1    Jan. 22, 2004

Related U.S. Application Data

(62) Division of application No. 09/810,379, filed on Mar. 16, 2001, now Pat. No. 6,617,118, which is a division of application No. 09/520,225, filed on Mar. 7, 2000, now Pat. No. 6,596,849.

(60) Provisional application No. 60/136,522, filed on May 28, 1999.

(51) Int. Cl.
*A61K 39/00* (2006.01)
(52) U.S. Cl. ............... 424/133.1; 424/138.1; 424/141.1; 424/155.1; 424/179.1; 424/180.1
(58) Field of Classification Search ............ 424/138.1, 424/141.1, 155.1, 179.1, 180.1
See application file for complete search history.

(56) References Cited

U.S. PATENT DOCUMENTS 4,427,653 A * 1/1984 Springer .............. 435/70.21
6,077,499 A * 6/2000 Griffiths et al. ............ 424/1.49

OTHER PUBLICATIONS

Cheng et al. (Cancer Imunol. Immunother. 1997; 44: 305-315).*
Cheng et al. (Bioconjugate Chem. 1999; 10: 520-528).*
Richter et al. (Int. Archs Allergy Appl. Immun. 1983: 70; 124-131).*
Hershfield et al. (Proc. Natl. Acad. Sci. 1991; 88: 7185-7189).*
Melton et al. (Journal of the National Cancer Institute 1996; 88: 153-165).*
Jung et al. (Mini Reviews in Medicinal Chemistry 2001; 1: 399-407).*
Klibanov et al., "Blood Clearance of Radiolabeled Antibody: Enhancement by Lactosamination and Treatment with Biotin-Avidin or Anti-Mouse IgG Antibodies", pp. 1951-1956, *The Journal of Nuclear Medicine*, vol. 29, No. 12, Dec. 1988.
Yao et al., "Improved Targeting of Radiolabeled Streptavidin in Tumors Pretargeted with Biotinylated Monoclonal Antibodies through an Avidin Chase", pp. 837-841, *The Journal of Nuclear Medicine*, vol. 36, No. 5, May 1995.

Guermant et al., "Quantitative Determination of Polyethylene Glycol Based Upon Its Salting Out and Partioning of a Dye into the Resulting Aqueous Two-Phase System", pp. 254-258, *Analytical Biochemistry* 230, (1995).
Kerr et al., "Application of Monoclonal Antibodies Against Cytosine Deaminase for the In Vivo Clearance of a Cytosine Deaminase Immunoconjugate", pp. 353-357, *Bioconjugate Chem.*, vol. 4, No. 5, (1999).
Pedley et al., "The Effect of Second Antibody Clearance on the Distribution and Dosimetry of Radiolabelled Anti-Cea Antibody in a Human Colonic Tumor Xenograft Model", pp. 713-718, *Int. J. Cancer* 43, (1989).
Sharkey et al., "Enhanced Clearance of Radiolabeled Murine Monoclonal Antibody by a Syngeneic Anti-idiotype Antibody in Tumor-Bearing Nude Mice", pp. 266-273, *Int. J. Cancer*, 51 (1992).
Kinahan et al., "High-Performance Liquid Chromatographic Determination of PEG 600 in Human Urine", pp. 297-307, *Journal of Chromatography*, 565, (1991).
Ruddy et al., "High-Performance Liquid Chromatographic Method for the Simultaneous Determination of Low-Molecular-Mass Oligomers of Polyethylene Glycol in Aqueous Skin Extracts", pp. 83-92, *Journal of Chromatography B.*, 657 (1994).
Kobabayshi et al., "Comparison of the Chase Effects of Avidin, Streptavidin, Neutravidin, and Avidin-Ferritin on a Radiolabeled Biotinylated Anti-Tumor Monoclonal Antibody", pp. 310-314, *Jpn. J. Cancer Res.*, 86, Mar. 1995.
Zhang et al., "Intravenous Avidin Chase Improved Localization of Radiolabeled Streptavidin in Intraperitoneal Xenograft Pretargeted With Biotinylated Antibody", pp. 61-64, *Nuclear Medicine & Biology*, vol. 24 (1997).
Sharkey et al., "Second Antibody Clearance of Radiolabeled Antibody in Cancer Radioimmunodetection", pp. 2843-2846, *Proc. Natl. Acad. Sci. USA*, vol. 81, May 1985.
Nag et al., "A Colorimetric Assay for Estimation of Polyethylene Glycol and Polyethylene Glycolated Protein Using Ammonium Ferrothiocyanate", pp. 224-231, *Analytical Biochemistry*, 237, (1996).
Cheng et al., "Accelerated Clearance of Polyethylene Glycol-Modified Proteins by Anti-Polyethylene Glycol IgM", pp. 520-528, *Bioconjugate Chemistry*, vol. 10, No. 3, 1999.
Cheng et al., "Efficient Clearance of Poly(ethylene glycol)- Modified Immunoenzyme with Anti PEG Monoclonal Antibody for Prodrug Cancer Therapy", pp. 258-266, *Bioconjugate Chemistry*, vol. 11 No. 2 (2000).

(Continued)

*Primary Examiner*—Shanon Foley
*Assistant Examiner*—Brandon Fetterolf
(74) *Attorney, Agent, or Firm*—Cohen Pontani Lieberman & Pavane LLP

(57) ABSTRACT

A novel anti-polyethylene glycol monoclonal antibody and its preparation are disclosed. Such an antibody can be used for determining polyethylene glycol concentration in vitro or accelerating the clearance of a polyethylene glycol containing compound from the blood circulation in the human body thereby reducing the toxicity associated with the polyethylene glycol containing conjugate. The antibody is particularly useful in cancer therapy where the therapeutic agent is selectively delivered to the tumor by increasing the tumor/blood ratio of the polyethylene glycol containing compound.

15 Claims, 17 Drawing Sheets

OTHER PUBLICATIONS

Rogers et al., "Plasma Clearance of an Antibody-enzyme Conjugate in ADEPT by monoclonal Anti-Enzyme: Its Effect on Prodrug Activation in vivo", pp. 1357-1363, *British Journal of Cancer*, 72, (1995).

Ryan et al., "Separation and Quantitation of Polyethylene Glycols 400 and 3350 from Human Urine by High Performance Liquid Chromatography", pp. 350-351, *Journal of Pharmaceutical Sciences*, 351, vol. 81, No. 4, Apr. 1992).

Marshall et al., "Galactosylated Streptavidin for Improved Clearance of Biotinylated Intact and F(ab')2 Fragments of an Anti-Tumor Antibody", pp. 18-24, *British Journal of Cancer*, 71, (1995).

Sharma et al., "Inactivation and Clearance of an Anti-CEA Carboxypeptidase G2 Conjugate in Blood After Localization in a Xenograft Model", pp. 659-662, *British Journal of Cancer*, 61, (1990).

Stocks, et al., "A Fluorometric Assay of the Degree of Modification of Protein Primary Amines with Polyethylene Glycol", pp. 232-234, *Analytical Biochemistry*, 154, (1986).

* cited by examiner

MONOCLONAL ANTIBODY FOR ANALYSIS AND CLEARANCE OF POLYETHYLENE GLYCOL AND POLYETHYLENE GLYCOL-MODIFIED MOLECULES

RELATED APPLICATIONS

This application is a divisional of U.S. patent application Ser. No. 09/810,379, filed on Mar. 16, 2001 now U.S. Pat. No. 6,617,118, which is a divisional of U.S. patent application Ser. No. 09/520,225, filed on Mar. 7, 2000 now U.S. Pat. No. 6,596,849, which claimed priority from U.S. Provisional Patent Application No. 60/136,522, filed on May 28, 1999, each of which is incorporated by reference.

BACKGROUND OF THE INVENTION

1. Field of the Invention

The present invention generally relates to a novel antibody against polyethylene glycol (PEG) and a process of using this novel antibody to accelerate the clearance of polyethylene glycol conjugates in the human body in cancer therapy as well as a method to quantify the concentration of PEG modified compounds.

2. Description of the Related Art

Recombinant proteins are increasingly being employed for the therapy of a wide variety of diseases (Nemunaitis, 1997; Fareed et al., 1998; Hudson, 1998; Lin, 1998; Harker, 1999; Sandborn and Hanauer, 1999). Many of the proteins in clinical development are modified by the covalent attachment of methoxypoly(ethylene glycol) (PEG) (Menzel et al., 1993; Basser et al., 1996; Fareed et al., 1998; Goffin et al., 1999; Harker, 1999), a flexible, linear polymer containing repeating —[OCH$_2$CH$_2$]— subunits (Delgado et al., 1992). PEG-modified proteins often exhibit prolonged circulation half-lives (Beckman et al., 1988; Cheng et al., 1997; Chapman et al., 1999) and reduced proteolytic cleavage (Roseng et al., 1992; Kaneda et al., 1995; Brinckerhoff et al., 1999). Immune responses against proteins can also be decreased by covalent attachment of PEG (Abuchowski et al., 1977a). Reduction of immunogenicity can be an important consideration because even recombinant human proteins can induce a humoral immune response (Atkins et al., 1986; Gribben et al., 1990). Conjugates formed between drugs and PEG have also recently been developed (Caliceti et al., 1993; Conover et al., 1997; Greenwald et al., 1998; Pendri et al., 1998). In addition, covalent attachment of PEG to liposomes has been found to reduce non-specific uptake as well as increase liposome stability and half-life (Kirpotin et al., 1997; Cabanes et al., 1998; Meyer et al., 1998).

Clinical development of PEG-modified proteins requires measurement of the pharmacokinetics in animals and patients. Ideally, the concentration of intact PEG-modified protein should be measured. Simple methods to measure intact PEG-protein conjugates, however, are not available. Analysis of PEG-modified proteins has been problematic (Delgado et al., 1992). Sodium dodecylsulfate polyacrylamide gel electrophoresis can be used to measure the relative size of PEG-modified proteins, but the mobility of PEG-modified proteins is slower than the expected molecular weight (Suzuki et al., 1984; Katre et al., 1987). Conjugates can be indirectly measured by first radiolabeling the protein (Kaneda et al., 1995; Cheng et al., 1997; Yabe et al., 1999) or PEG (Mullin et al., 1997), but radioisotopes pose safety concerns and require special handling. Functional assays can be employed to measure the concentration of the protein component of conjugates (Cheng et al., 1997; Esslinger et al., 1997), but no information is provided about the stability of covalently attached PEG chains. Methods that measure the number of PEG molecules attached to a protein (Habeeb, 1966; Stocks et al., 1986) require that purified conjugate be employed which is difficult to achieve in pharmacokinetic studies. Methods that directly measure the concentration of PEG are relatively insensitive. Colorimetric methods based on complex formation between barium-iodide and PEG require that proteins are first removed and have detection limits of around 1-5 µg PEG (Childs, 1975). A colorimetric method based on partitioning of a chromophore present in aqueous ammonium ferrothiocyanate reagent can be employed for complex protein mixtures but has a detection limit of 1-5 µg PEG (Nag et al., 1996; Nag et al., 1997). High performance liquid chromatography can detect PEG with a detection limit around 1-5 µg/ml (Kinahan and Smyth, 1991; Ryan et al., 1992; Ruddy and Hadzija, 1994; Miles et al., 1997). Phase-partitioning can be employed to measure PEG but the assay sensitivity is about 1 µg PEG (Guermant et al., 1995). Finally, polyclonal antibodies against PEG can detect the presence of 1 µg/ml PEG in PEG-modified proteins (Richter and Akerblom, 1983).

The development of monoclonal antibodies against PEG could allow quantitation of PEG and PEG-modified proteins by standard immunoligical assays including ELISA, immunoblotting, dot blotting and radioimmunoassay. It is difficult, however, to produce antibodies against PEG due to its ability to modulate immune responses. For example, immune responses against proteins are often decreased by covalent attachment of PEG (Abuchowski et al., 1977b). PEG modification has been shown to reduce the immunogenicity of enzymes (Abuchowski et al., 1977a; Chaffee et al., 1992), antibodies (Kitamura et al., 1991), toxins (Wang et al., 1993; He et al., 1999), recombinant human proteins (Katre, 1990) and other proteins (Chinol et al., 1998). PEG-modified proteins often induce tolerance to the unmodified protein in many (Lee et al., 1981; Savoca et al., 1984; Maiti et al., 1988; Saito et al., 1996; Ito et al., 1997; Ito et al., 1998), but not all cases (Savoca et al. 1979; Chen et al., 1981). Rabbit polyclonal antibodies against PEG have been generated by immunizing rabbits with PEG linked to different proteins (Richter and Akerblom, 1983). PEG alone did not generate an immune response. PEG linked to bovine superoxide dismutase or ragweed pollen extract did not reproducibly generate an anti-PEG response even when the imunogens were given in Freund's complete adjuvant. PEG-modified ovalbumin in Freund's complete adjuvant produced an antibody response in most but not all animals. Antisera raised against PEG-modified ovalbumin could detect PEG-modified proteins with a limit of detection of approximately 1 µg/ml (Richter and Akerblom, 1983). However, no monoclonal antibodies have been successfully produced against PEG to date. Monoclonal antibodies possess advantages compared to polyclonal anti-serum for standardized assays including the ability to produce unlimited quantities of homogeneous antibody with consistent binding affinity.

A major goal of anti-tumor drug development is to increase the therapeutic index of chemotherapy, thereby improving treatment efficacy. One approach to increase the therapeutic index of chemotherapy is to preferentially activate antineoplastic prodrugs at cancer cells but not normal tissues. Tumor selectivity may be achieved by enzymatically converting prodrugs possessing low toxicity to highly toxic anti-neoplastic agents by previously administered antibody-enzyme conjugates (immunoenzymes) that have been allowed to accumulate at tumor cells (Bagshawe et al., 1988; Senter et al., 1988). Even though maximum accumulation of immunoenzymes in tumors occurs around 24 h after administration (Bosslet et al., 1994; Wallace et al., 1994), prodrugs are generally administered from 3-7 days (Bosslet et al., 1994; Svensson et al., 1998) to up to 2 weeks (Eccles et al., 1994) later to allow adequate time for conjugate to clear from the blood, thereby minimizing systemic prodrug activation and associated toxicity to normal tissues. The requisite of low circulating levels of immunoenzyme therefore often precludes prodrug administration when maximum localization has been achieved.

Prodrugs can be administered during the period of maximum tumor accumulation of immunoenzymes if circulating conjugates are removed or deactivated. Several methods have been devised to accelerate the clearance of radioimmunoconjugates and immunoenzymes from the circulation including the administration of polyclonal (Stewart et al., 1990) and anti-idiotypic antibodies (Ullen et al., 1995a; Ullen et al., 1995b) against the antibody portion of the immunoconjugate, injection of avidin to clear biotinylated antibodies (Klibanov et al., 1988; Paganelli et al., 1991; Stella et al., 1994; Kobayashi et al. 1995), use of monoclonal antibodies against enzymes to clear (Kerr et al., 1993; Haisma et al., 1995) or deactivate (Sharma et al., 1990) immunoenzymes, and extracorporeal immunoadsorption (Tennvall et al., 1997) to remove immunoconjugates from plasma.

β-Glucuronidase targeted to tumor cells can activate the glucuronide prodrug (BHAMG) of p-hydroxy aniline mustard (pHAM) in vitro (Wang et al., 1992) and cure advanced hepatoma ascites in a rat model (Chen et al., 1997). Antibody-βG conjugates injected intravenously, however, are rapidly cleared from the circulation before significant tumor accumulation occurs (Cheng et al., 1997). Modification of βG with PEG can extend the half-life of antibody-βG conjugates, decrease the normal tissue uptake, and increase the localization of the conjugate at the solid tumors in nude mice (Cheng et al., 1997). Although the extended half-life of PEG-modified βG conjugate is desirable for improved tumor uptake, at least five days were required for the serum concentration of the conjugates to reach a safe level before a prodrug could be administered (Cheng et al., 1997). The accelerated clearance of conjugates from the circulation may allow earlier prodrug administration when the maximum amount of the conjugate is present at tumor cells. We generated mAbs against βG and PEG and examined their effects on the clearance of the βG-sPEG conjugates. The effect of incorporating galactose residues in the clearing antibodies was also examined because galactose can accelerate the removal of proteins from the circulation (Thornburg et al., 1980) by the hepatic asialoglycoprotein receptor (Ong et al., 1991). Rapid clearance of an antibody-carboxypeptidase G2 conjugate by a galactose-modified antibody (Sharma et al., 1990; Sharma et al., 1994) allowed earlier administration of a prodrug with reduced toxicity (Rogers et al., 1995). In addition, galactose-modified mAb has also been employed in a clinical trial to remove residual antibody-carboxypeptidase G2 conjugate from the circulation before prodrug administration (Martin et al., 1997).

SUMMARY OF THE INVENTION

We have produced a monoclonal antibody AGP3 that binds to polyethylene glycol (PEG) by immunizing mice with a conjugate (RH1-βG-PEG) in which PEG-modified beta-glucuronidase (βG) was covalently attached to a murine immunoglobulin (mAb RH1). Fusion of myeloma cells with spleen cells isolated from mice immunized with RH1-βG-PEG without adjuvant resulted in the isolation of a hybridoma secreting an IgM monoclonal antibody to PEG. Such a monoclonal antibody is useful for quantifying the concentration of PEG or PEG-containing compounds in a sample in vitro.

In the present application, we have also developed a clearance system for PEG-modified compounds (Cheng et al., 1999; Cheng et al., In press) for use in cancer therapy through antibody-directed enzyme activation of glucuronide prodrugs. We have found that an IgM antibody against PEG can satisfactorily clear PEG-containing compounds from the circulation without significant toxic side-effects.

PEG-containing proteins often exhibit extended serum half-lives, reduced immunogenicity and decreased susceptibility to proteolytic degradation (Delgado et al., 1992). Antibody fragments and immunoconjugates that have been modified with PEG also display reduced normal tissue uptake and enhanced tumor accumulation (Pedley et al., 1994; Delgado et al., 1996; Cheng et al., 1997). Clearance of PEG-modified immunoconjugates with AGP3 may therefore be generally useful. We examined whether AGP3 could improve tumor-blood ratios and allow earlier administration of a prodrug in a preclinical model of human colorectal carcinoma.

Accordingly, an object of the present invention is directed to a novel anti-PEG antibody and the preparation thereof.

Another object of the present invention is directed to develop an immunoassay to identify or quantify PEG in a sample, using an anti-PEG monoclonal antibody.

A further object of the present invention is directed to a method of treating a cancer patient, which comprises the steps of:

a. administering a PEG-containing compound comprising tumor targeting means and means for activating an anti-tumor prodrug to the patient;

b. administering an anti-polyethylene glycol antibody to the patient to accelerate the clearance of the PEG-containing compound from the blood circulation after step a; and c. administering the anti-tumor prodrug to said patient after step b.

In a preferred embodiment, PEG-modified βG was covalently linked to the F(ab')$_2$ fragment of mAb B72.3, an IgG$_1$ antibody that binds to TAG-72 antigen expressed on the majority of colon adenocarcinomas, invasive ductal carcinomas of the breast, non-small cell lung carcinomas, common epithelial ovarian carcinomas, and gastric, pancreatic and esophageal cancers with limited reactivity to normal adult tissues (Thor et al., 1986). $^{111}$In-labeled B72.3 (Cyt-103) is approved for clinical use as an imaging agent for colorectal and ovarian carcinoma (Divgi et al., 1994). We have showed that clearance of a PEG-modified B72.3 immunoenzyme with AGP3 produced higher tumor-blood ratios without sacrificing tumor accumulation, allowing earlier prodrug administration with minimal toxicity.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

DETAILED DESCRIPTION OF THE PRESENTLY PREFERRED EMBODIMENTS

Figure 1:
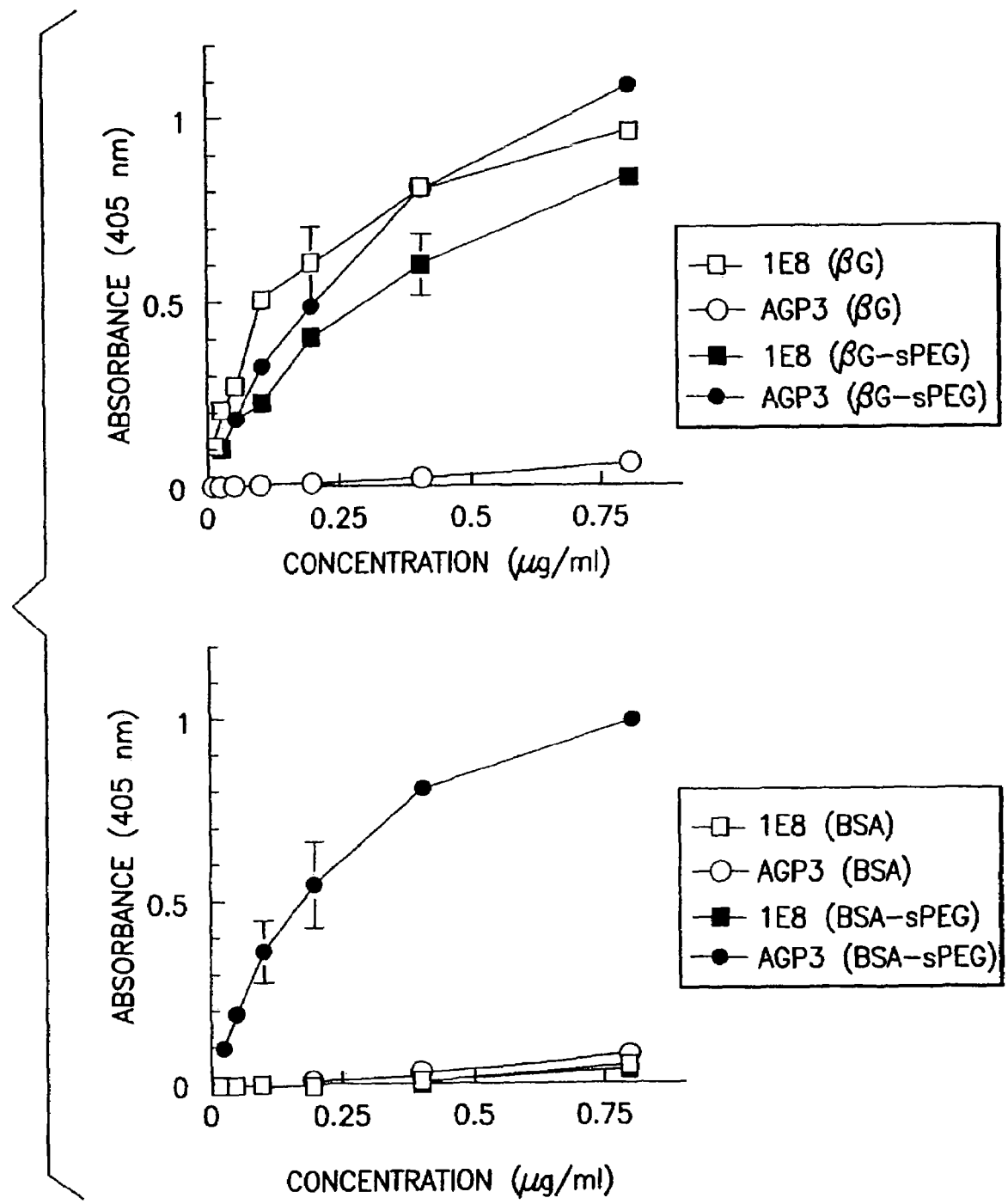
FIG. 1 shows binding specificity of antibodies 1E8 and AGP3.

Abbreviations:

1E8-xG, mAb 1E8 containing x galactose moieties per antibody.

5A8-PEG, conjugate formed between mAb 5A8 and βG-sPEG.

AGP3-biotin, mAb AGP3 derivatized with biotin.

AGP3-xG, monoclonal antibody AGP3 containing x galactose groups per antibody.

B72.3-β-PEG, conjugate of the F(ab')$_2$ fragment of mAb B72.3 with βG-sPEG.

βG, Eschericia coli β-glucuronidase.

βG-PEG-βG, β-glucuronidase crosslinked with poly(ethylene glycol)-di-succinimidyl succinamide.

βG-pPEG, β-glucuronidase modified with pPEG.

βG-sPEG, β-glucuronidase modified with sPEG.

βG-tPEG, β-glucuronidase modified with tPEG.

BMAMG, glucuronide prodrug of pHAM.

BSA, bovine serum albumin.

BSA-sPEG, bovine serum albumin modified with sPEG.

ELISA, enzyme-linked immunosorbent assay.

H25-βG-PEG, conjugate of the F(ab')$_2$ fragment of mAb H25B10 with βG-sPEG.

HRP, horse-radish peroxidase.

HRP-GAM, horse-radish peroxidase conjugated goat anti-mouse antibody.

HRP-GAM μ-chain, horse-radish peroxidase conjugated goat anti-mouse IgM μ-chain antibody.

IC$_{50}$, drug concentration causing 50% inhibition of cellular protein synthesis.

mAb, monoclonal antibody.

PBS, phosphate-buffered saline.

PBS-T, PBS containing 0.05% Tween-20.

PEG, monomethoxy poly(ethylene glycol).

PEG-(SSA)$_2$, poly(ethylene glycol)-di-succinimidyl succinamide pHAM, p-hydroxy aniline mustard.

PNPG, p-nitrophenol β-D-glucuronide.

pPEG, methoxypoly(ethylene glycol) succinimidyl propionate.

PLT, platelets.

RBC, red blood cells.

RH1-βG-PEG, conjugate formed between mAb RH1 and βG-sPEG.

SDS-PAGE, sodium dodecyl sulfate-polyacrylamide gel electrophoresis.

SMCC, succinimidyl-4-[N-malemidomethyl]cyclohexane-1-carboxylate.

sPEG, methoxypoly(ethylene glycol) succinimidyl succinate.

TAG-72, tumor-associated glycoprotein.

tPEG, methoxypoly(ethylene glycol) tresylate.

WBC, while blood cells.

Definitions:

As hereinafter used, the term "conjugate" means a complex formed by chemically-linking two or more proteins; the term "derivatize" means chemically linking a small molecular weight compound to a protein; the term "modify" means chemically linking a chemical such as PEG or galactose to the surface of a protein.

Murine hybridoma cell line AGP3 was deposited pursuant to the Budapest Treaty with the China Center for Type Culture Collection (CCTCC) on Jan. 13, 2000, and assigned deposit number CCTCC-V-200001. The CCTCC is located at Wuhan University, Wuhan 430072, P.R. China. This cell line was isolated from a fusion between FO myeloma cells and BALB/c spleen cells, and secretes an IgM monoclonal antibody.

Experimental Procedures

Materials: BSA (Fraction V), methoxypoly(ethylene glycol) succinimidyl succinate (sPEG, MW 5000), methoxypoly(ethylene glycol) tresylate (tPEG, MW 5000), cyanomethyl-2,3,4, 6-tetra-O-acetyl-1-thio-β-D-galactopyranoside, Ultrogel AcA 22, trinitrobenzenesulfonic acid, fluorescamine, and p-nitrophenyl β-D-glucuronide were purchased from Sigma Chemical Co. (St. Louis, Mo.). Methoxypoly (ethylene glycol) succinimidyl propionate (pPEG, MW 5000) was obtained from Fluka (Buchs, Switzerland). Poly(ethylene glycol)-di-succinimidyl succinamide (PEG-(SSA)$_2$, MW 3,4000) was purchased from Shearwater Polymers (Huntville, Ala.). Succinimidyl-6-(biotinamido) hexanoate (NHS-LC-biotin) was obtained from Pierce (Rockford, Ill.). Sephacryl S-200 HR, Sephacryl S-300 HR and Sephadex G-25 gels were from Pharmacia Biotech Asia Pacific Ltd. (Taiwan). pHAM and BHAMG were synthesized as described (Roffler et al., 1991). Succinimidyl-4-[N-maleimidomethyl]cyclohexane-1-carboxylate (SMCC) was from Pierce Chemical Company, Rockford, Ill.

Cells: LS174T colon adenocarcinoma cells (ATCC CL-188) were obtained from the American Type Culture Collection (Rockville, Md.). Cells were mycoplasma free and cultured in Dulbecco's modified Eagle's medium (Gibco BRL, Grand Island, N.Y.) supplemented with 10% heat-inactivated bovine serum, 100 U/ml penicillin and 100 μg/ml streptomycin. FO myeloma cells (ATCC CRL-1646) were purchased from the American Type Culture Collection (Manassas, Va.).

Animals: BALB/c mice were obtained from the animal room of the Institute of Biomedical Sciences, Academia Sinica. BALB/c nu/nu mice were from the Cancer Research Laboratory, Tri-Service General Hospital, Taipei. Animal experiments were performed in accordance with institute guidelines.

Apparent to those ordinarily skilled in the art, any of the above described materials, cell lines or animals may be substituted by other like materials, cell lines, animals or their equivalents, produced by any manufacturer, to perform substantially the same functions.

Antibodies: mAb RHI, an $IgG_2$, mAb that binds to an antigen expressed on the surface of AS-30D rat hepatoma cells, was generated as described (Roffler et al., 1994). Hybridomas secreting mAb B72.3 (ATCC HB-8108), an $IgG_1$ monoclonal antibody specific to the tumor-associated glycoprotein (TAG-72) antigen (Johnson et al., 1986) and mAb H25B10 (ATCC CRL-8017), a control $IgG_1$ antibody that binds to the surface antigen of hepatitis B virus, were obtained from the American Type Culture Collection. mAb 5A8, an $IgG_{2a}$ mAb that binds to the surface immunoglobulin expressed on 38C13 lymphoma cells (Maloney et al., 1985), was provided by Dr. Mi-Hua Tao, Institute of Biomedical Sciences, Academia Sinica. mabs were purified from ascites by affinity chromatography on Sepharose-protein A in high salt buffer. The F(ab')$_2$ fragments of mAb B72.3 and H25B10 were generated by proteolytic digestion of whole antibodies with bromelian (Milenic et al., 1989). F(ab')$_2$ fragments were purified by sequential chromatography on DE-52 (anion exchange) and Sephacryl S-200 HR (gel filtration). Streptavidin-HRP (horse radish peroxidase) was from Scrotec (Oxford, UK). HRP-conjugated goat anti-mouse IgM μ-chain antibody (HRP-GAM μ-chain) and HRP-conjugated goat anti-mouse IgG (HRP-GAM) were from Organon Teknika (Durham, N.C.).

PEG-Modification of βG: Recombinant *Eschericia coli*-derived βG was produced and purified as described (Cheng et al., 1997). Twenty milligrams of sPEG per milligram of βG (2 mg/mL) were mixed in coupling buffer (deoxygenated PBS containing 1 mM EDTA, pH 8.0) at room temperature for 2 h before one-tenth the volume of a saturated glycine solution was added to stop the reaction. Unreacted PEG was removed by dialysis against PBS or by gel filtration on a 2.5×100 cm Sephacryl S-200 HR column eluted with PBS at 15 mL/h. Relevant fractions were pooled and concentrated by ultrafiltration to 1.5-2.0 mg/mL for storage at −80° C. BSA was modified with sPEG in a similar manner. In some experiments, βG in coupling buffer was modified with 2 mg of sPEG or with 2 or 20 mg of tPEG/mg of βG.

To produce βG-pPEG, βG was passed through a 2.5×30 cm Sephadex G-25 column equilibrated with 0.1 M borate buffer, pH 8.0 and concentrated by ultrafiltration to 3 mg/ml Ten milligrams pPEG in 0.1 M borate buffer, pH 8.0 (150 mg/ml) was added per mg βG and mixed for 2 h at room temperature before one-tenth volume of a saturated solution of glycine was added to stop the reaction. Unreacted PEG was removed by gel filtration on a 2.5×100 cm Ultrogel AcA 22 column eluted with PBS at 15 ml/h. Relevant fractions containing βG-PEG were pooled and concentrated by ultrafiltration to 1 mg/ml for storage at −80° C. βG was crosslinked with PEG-(SSA)$_2$ (3.3 mg PEG per mg βG) in a similar manner to produce βG-PEG-βG.

Protein concentrations were determined by the bicinchoninic acid assay (Pierce, Rockford, Ill.) with BSA employed as the reference protein. The BCA assay was not affected by covalently coupled PEG after removal of free PEG.

Conjugation of antibodies to βG-sPEG: mAb RH1 and 5A8 were passed through a 2.6×30 cm Sephadex G-25 column equilibrated with coupling buffer and concentrated by ultrafiltration to 3 mg/ml. A 4-fold molar excess of SMCC (1 mg/mL in dioxane) was slowly added to the antibodies and allowed to react at room temperature for 50 min. Unreacted SMCC was removed by gel filtration on a 2.6×30 cm Sephadex G-25 column equilibrated with coupling buffer. Typically, an average of 1 to 1.5 maleimido groups was introduced into antibodies. βG-sPEG was partially reduced by adding dithiothreitol to a final concentration of 20 mM for 1 h at 37° C. Freshly derivatized antibody and βG-sPEG were immediately mixed at an equal molar ratio, concentrated to 2 mg/mL by ultrafiltration and incubated at room temperature for 2 h. Cysteine was added to a final concentration of 2 mM to stop the reaction and the mixture was concentrated by ultrafiltration to about 5 mg/mL. Conjugates were purified on a 2.5×100 cm Sephacryl S-300 HR column equilibrated with PBS at a flow rate of 15 mL/h. Fractions containing conjugate monomers (antibody/enzyme=1:1) were pooled and concentrated by ultrafiltration to 1.5-2.0 mg/mL for storage at −80° C. The yield of conjugates averaged around 35% based on the weight of the purified conjugate divided by the total starting weights of antibody and enzyme.

mAb B72.3-F(ab')$_2$ and mAb H25-F(ab')$_2$ were also linked to βG-sPEG by the procedure described above to produce the conjugates B72.3-βG-PEG and H25-βG-PEG. Conjugates were purified by size exclusion chromatography on Sephacryl S-300 HR equilibrated with PBS. The antigen-binding activity of conjugates were measured by ELISA in 96-well microtiter plates coated with bovine submaxillary gland mucin (King et al., 1994). The combined antigen-binding and enzymatic activities were measured as described (Chen et al., 1997).

Generation of Monoclonal Antibodies against βG and βG-PEG: Generally, monoclonal antibodies against a PEG molecule or moiety may be produced by conjugating the PEG molecule with an antigenic molecule, such as a protein. Immunization of mice with such conjugated PEG to produce desired antibodies can be routinely performed by a person of ordinary skill in the art. Preferably, the conjugated PEG is linked with another molecule to form a three-part complex for immunization of mice. Most preferably, female BALB/c mice were i.v. injected with 200 μg of RH1-βG-PEG in PBS on day 1 and i.p. injected with 100 μg of RH1-βG-PEG on days 7, 14, 21 and 28. Mice received a final i.v. injection of 200 μg of RH1-βG-PEG on day 54. Hybridomas were generated by fusing spleen cells with FO myeloma cells 3 days later (Yeh et al., 1979). Hybridomas were screened by ELISA in 96-well microtiter plates coated with βG or βG-PEG. Positive hybridomas were cloned by limiting dilution in 96-well plates containing thymocyte feeder cells in HT medium supplemented with 15% fetal calf serum. The isotypes and subclasses of mAbs were determined with the Mouse MonoAb-ID kit according to the manufacturer's instructions (Zymed laboratories, South San Francisco, Calif.). The apparent affinities of antibodies were measured as described (Beatty et al., 1987).

Purification of AGP3: AGP3 ascites obtained from pristane-primed eight-week old BALB/c female mice was centrifuged at 5000 g for 10 min to remove debris. Ascites fluid (5 ml) was passed through a 5 ml Sephadex G-25 column equilibrated with PBS and then purified by gel filtration on a 2.5×100 cm Ultrogel AcA 22 column eluted with PBS at 15 ml/h. Fractions containing AGP3 were collected, concentrated by ultrafiltration to 1-2 mg/ml and stored at −80° C. Yields of 5-6 mg AGP3 per ml ascites were typically achieved.

Biotinylation of AGP3: AGP3 (1 mg/ml) in 0.1 M borate buffer, pH 8.0 was mixed with a 25-fold molar excess of NHS-LC-biotin for 1 h at room temperature to produce AGP3-biotin. One-tenth volume of a saturated solution of glycine was added to stop the reaction before aliquots were stored at −80° C. The antigen-binding activity of AGP3-biotin was determined by ELISA in 96-well microplates coated overnight with 1 μg/well βG-tPEG (20 mg tPEG per mg βG). Plates were blocked 1 h at 37° C. with 2% skim milk in PBS before 50 μL/well samples of AGP3 or AGP3-biotin in dilution buffer (0.5% BSA, 0.05% Tween-20 in PBS) were added to the wells for 1 h at room temperature. Plates were washed 6 times with PBS/TB (0.05% bovine serum albumin, 0.1% Tween-20 in PBS) and 50 μL/well of either streptavidin-HRP (1:1000) or HRP-GAM μ-chain (1:1000) in dilution buffer were added for 1 h at room temperature. The plates were washed 6 times and 100 μL/well ABTS substrate (0.4 mg/ml 2,2'-azino-di(3-ethyl-benzthiazoline-6-sulfonic acid), 0.003% $H_2O_2$, 100 mM phosphate-citrate, pH 4.0) was added for 30 min at room temperature. Absorbance (405 nm) of wells was measured in a Molecular Devices (Menlo Park, Calif.) microtiter plate reader.

Radiolabeling of AGP3: AGP3 may be radiolabeled by a radioactive isotope such as $^{125}I$ or $^{131}I$. Any established method such as a method of iodination suitable for radiolabeling a monoclonal antibody may be used for labeling AGP3.

AGP3 ELISA: Maxisorp™ 96-well microplates (Nunc™, Roskilde, Denmark) were coated with 50 μL/well of AGP3 (200 μg/ml in PBS) for 3 h at 37° C. Plates were blocked with 2% skim milk in PBS overnight and washed twice with PBS/T (0.05% Tween-20 in PBS) before serial dilutions of βG or βG-pPEG (50 μL in dilution buffer) were added to wells for 1.5 h at room temperature. Plates were washed 6 times with PBS/T and 50 μL/well AGP3-biotin (20 μg/ml in dilution buffer) was added for 1.5 h at room temperature. Plates were again washed with PBS/T and 50 μL/well streptavidin-HRP (1:1000) was added for 1 h at room temperature. Plates were washed before 100 μL/well ABTS substrate was added for 30 min at room temperature. Absorbance (405 nm) of wells was measured in a microtiter plate reader. The effect of serum on the AGP3 ELISA was examined by performing the assay in the presence of 10% serum isolated from healthy BALB/c mice.

The affinities of AGP3 to various PEG molecules were examined using ELISA. Generally, AGP3 may bind any PEG molecule with a tendency that its affinities to those PEG molecules increase with PEG's molecular weights, i.e., the higher the PEG molecular weight, the better AGP3 will bind. Preferably, AGP3 binds PEG molecules having molecular weights ranging from 3,000 to 60,000 daltons, and molecular weights ranging from 5,000 to 60,000 daltons are most preferred.

Pharmacokinetics of βG-pPEG: Male BALB/c mice were i.v injected with 150 μg βG-pPEG. Serum was isolated from blood samples that were periodically removed from the tail vein of the mice. The concentration of βG-pPEG in serially-diluted serum samples was assayed in triplicate by the AGP3 ELISA. The concentration of βG-pPEG was determined by comparison to a standard curve generated with known concentrations of βG-pPEG.

Immunoblotting of PEG-Modified Proteins: Samples were electrophoresed in sodium-dodecyl polyacrylamide gels under reducing conditions before overnight transfer to nitrocellulose paper by passive diffusion in blotting buffer (50 mM NaCl, 2 mM EDTA, 0.5 mM 2-mercapto-ethanol, and 10 mM Tris-HCl, pH 7.5). Blots were blocked with 5% skim milk and incubated for 1 h at 37° C. with 1E8 or AGP3 ascites diluted 1:2000 in PBS containing 0.05% BSA. Blots were washed 3 times with PBS-T and twice with PBS before incubation with HRP-GAM or HRP-GAM μ-chain for 30 min at 37° C. Blots were washed and bands were visualized by ECL detection according to the manufacturer's instructions (Pierce, Rockford, Ill.).

Galactose-Modification of Antibodies: Cyano-methyl-2,3,4,6-tetra-O-acetyl-1-thio-β-D-galactopyranoside was reacted with 0.1 M sodium methoxide in dry methanol for 48 h (Marshall et al., 1995). The methanol was removed by evaporation under vacuum and 1E8 or AGP3 (5 mg/mL in pH 8.5 borate buffer) were directly added and allowed to react for 2 h. Different amounts of galactose were incorporated into antibodies by varying the ratio of the reactants. The number of galactose groups introduced into antibodies was estimated by the reduction of trinitrobenzenesulfonic acid reactive amine groups after galactose modification (Habeeb, 1966) using a molar extinction coefficient ($\epsilon^{335}$) of $1.31\times10^4$ for 1E8 and $1.38\times10^4$ for AGP3. Galactose groups were also estimated by measuring amine groups with flouorescamine before and after galactose modification (Stocks et al., 1986).

Serum Half-Lives of Galactose-Modified 1E8 and AGP3: BALB/c mice were i.v. injected with 200 μg. of unmodified or galactose-modified 1E8 or AGP3. Serum was isolated from blood samples that were periodically removed from the tail vein of mice. The concentrations of 1E8 or AGP3 were determined in duplicate samples by ELISA in microtiter plates coated with βG or βG-sPEG, respectively, by comparison to standard curves generated with known concentrations of the corresponding unmodified or galactose-modified antibodies.

Clearance of βG-PEG and 5A8-βG-PEG from Serum: Groups of 3 BALB/c mice were i.v. injected with βG-sPEG or 5A8-βG-PEG at time zero. Blood samples were periodically removed before i.v. injection of unmodified or galactose-modified 1E8 or AGP3 at 24 h. Additional blood samples were taken at subsequent times and the βG activity in duplicate samples was measured using p-nitrophenol β-D-glucuronide as substrate (Wang et al., 1992). Sample concentrations were calculated by comparison of absorbance values with standard curves constructed from known concentrations of βG-sPEG or 5A8-βG-sPEG. For meaningful comparison of clearance results, the measured concentrations of βG-sPEG in mice injected with clearing antibodies were normalized to the mean concentration of βG-sPEG in control (uncleared) mice just before clearance by $$N_j=(C_{mi}/C_i)C_j$$

where $N_j$ is the normalized serum concentration of βG-sPEG in an experimental mouse at time j, $C_{mi}$ is the mean serum concentration of βG-sPEG in the control group serum at the last time point before clearance, $C_i$ is the serum concentration of βG-sPEG in an experimental mouse at the last time point before clearance, and $C_j$ is the serum concentration of βG-sPEG in an experimental mouse at time j.

Toxicity of Clearance: The numbers of WBC, RBC, and PLT in groups of 6 BALB/c mice were measured as described (Chen et al., 1997) 1 day before i.v. injection of 50 μg of βG-PEG or PBS. Mice were i.v. injected 24 h later with 300 μg AGP3 or AGP3-208G. or 2 fractionated 150 μg doses of AGP3-208G separated by 4 h. After allowing 6 h for clearance, mice were i.v. injected with two 7.5 mg/kg doses of BHAMG in PBS. On day 8, the numbers of WBC, RBC, and PLT in serum samples were determined. On days 3 and 10, the spleen, liver and kidney were removed from one mouse in each group and fixed in 10% formalin. Ethanol dehydrated samples were embedded in paraffin and cut into 3 μm sections. Sections were then dewaxed with xylene, stained with hematoxylin/eosin, and dehydrated before observation under a light microscope. The weight of mice was followed for 18 days.

pH Dependence of βG Activity: Fifteen μL of βG (4 μg/mL) was mixed in microtiter plates with 200 μl of βG buffer (Wang et al., 1992) with pH values ranging from 3-10. Twenty-five μL of p-nitrophenol β-D-glucuronide (32 mM) was added to the wells at 37° C. for 15 minutes, excess 1N NaOH was added to adjust the pH to greater than 10, and absorbance was read at 405 nm in a microplate reader. To test the pH stability of βG, enzyme in βG buffer was adjusted to pH values ranging from 3-11 for 4 h at 37° C. before neutralization to pH 7.0 and assay of enzymatic activity.

Drug sensitivity of LS174T cells: LS174T cells were plated overnight in 96 well microtiter plates at 40,000 cells per well. Serial dilutions of pHAM or BHAMG in medium containing 10% fetal calf serum were added to cells in triplicate for 24 h at 37° C. Cells were subsequently washed once with sterile PBS, incubated until hour 48 in fresh leucine-free medium and then pulsed for 12 h with [$^3$H]-leucine (1 μCi/well) in fresh medium and harvested with a Filter-mate (Packard). Incorporated radioactivity was determined on a Top-Count scintillation counter (Packard). Results are expressed as percentage inhibition of [$^3$H]-leucine incorporation compared with untreated cells (control) by the following formula:

$$\% \text{ inhibition} = 100 \times \frac{\text{cpm sample} - \text{cpm background}}{\text{cpm control} - \text{cpm background}}$$

Radiolabeling of Conjugates: B72.3-βG-PEG and H25-βG-PEG were labeled with $^{125}$I Bolton-Hunter reagent to specific activities of 0.5-0.7 and 0.5-0.7 μCi/μg, respectively, according to the manufacturer's instructions (ICN Pharmaceuticals Inc., Costa Mesa, Calif.). Conjugates retained antigen-binding activity and specificity as determined by radioimmunoassay against bovine submaxillary gland mucin coated in 96-well microtiter plates. βG activity was unaffected and conjugates were not degraded as determined by gel autoradiography after sodium dodecyl sulfate polyacrylamide electrophoresis.

Tumor Localization of B72.3-βG-PEG: $5 \times 10^6$ LS174T cells were injected s.c. in 6-8 week old nude mice. After tumors had grown to approximately 100-200 mm$^3$, 200 μg (60 μCi) [$^{125}$I]B72.3-βG-PEG or [$^{125}$I]H25-βG-PEG were i.v. injected into the lateral tail vein of mice. Groups of 3-4 mice were sacrificed after 24, 48, 72 and 96 h. Tumors, blood and organs were weighed on an analytical balance and assayed for radioactivity in a multichannel gamma-counter. The results are expressed as the specific uptake of the conjugates by the tumor or the tissue (% injected dose/g).

In vivo Clearance of B72.3-βG-PEG and H25-βG-PEG: Groups of 4 BALB/c nu/nu mice were i.v. injected with 250 μg B72.3-βG-PEG or H25-βG-PEG at time zero. Blood samples were periodically removed before mice were given two i.v. injection of 300 and 200 μg of AGP3 at 48 and 50 h. Additional blood samples were taken at subsequent times and the βG activity in duplicate samples was measured using p-nitrophenol β-D-glucuronide as substrate (Wang et al., 1992). Sample concentrations were calculated by comparison of absorbance values with a standard curve constructed from known concentrations of B72.3-βG-PEG and H25-βG-PEG.

Tumor Localization of B72.3-βG-PEG after Clearance: $5 \times 10^6$ LS174T cells were injected s.c. in 6-8 week old nude mice. After 12 days, groups of 8 BALB/c nu/nu mice bearing 100-200 mm$^3$ LS174T tumor xenografts were i.v. injected at time 0 with 200 μg (140 μCi) [$^{125}$I] B72.3-βG-PEG or [$^{125}$I] H25-βG-PEG. Half of the mice were i.v. injected 48 and 50 h later with two fractionated 300 and 200 μg doses of AGP3 whereas PBS was given to the other half. Mice were sacrificed after allowing 6 h for clearance. Tumors, blood and organs were weighed on an analytical balance and assayed for radioactivity in a multichannel γ-counter. Results are expressed as specific uptake of conjugate in tumor or tissues (% injected dose/g).

Therapy of LS174T Tumor Xenografts: Groups of 9 BALB/c nu/nu mice were s.c. injected on the right flank with $5 \times 10^6$ LS174T cells on day 1. On day 10, mice were i.v. injected via the lateral tail vein with PBS, 250 μg B72.3-βG-PEG or 250 μg H25-βG-PEG. 48 and 50 h later mice were i.v. injected with 2 sequential doses of 300 and 200 μg AGP3. Mice were i.v. injected 6 h later with BHAMG (7.5 mg/kg×3). Control groups of tumor-bearing mice were treated with BHAMG (7.5 mg/kg×3), pHAM (2 mg/kg×3) or PBS alone. Therapy was repeated starting on days 16, 26, and 41. All mice received 2-4 rounds of therapy. Tumor volumes (length×width×height×0.5) were measured twice a week and mice weight was followed as an estimate of treatment toxicity. Mice were killed when they displayed signs of morbidity or when the tumor size exceeded 2.5 cm$^3$. Groups of 8 BALB/c nu/nu mice bearing larger 200-250 mm$^3$ tumors were also treated as above with 2 rounds of therapy starting on days 11 and 23.

Data Analysis: Statistical significance of differences between mean values was calculated with the shareware program Schoolstat (White Ant Occasional Publishing, West Melbourne, Australia) using the independent t-test for unequal variances.

The methods described above are illustrative. They shall not be construed as limitations to the present invention. The present invention encompasses any variations or modifications of the above described methods, which are known or would have been known to those ordinarily skilled in the art.

Results

Figure 8:
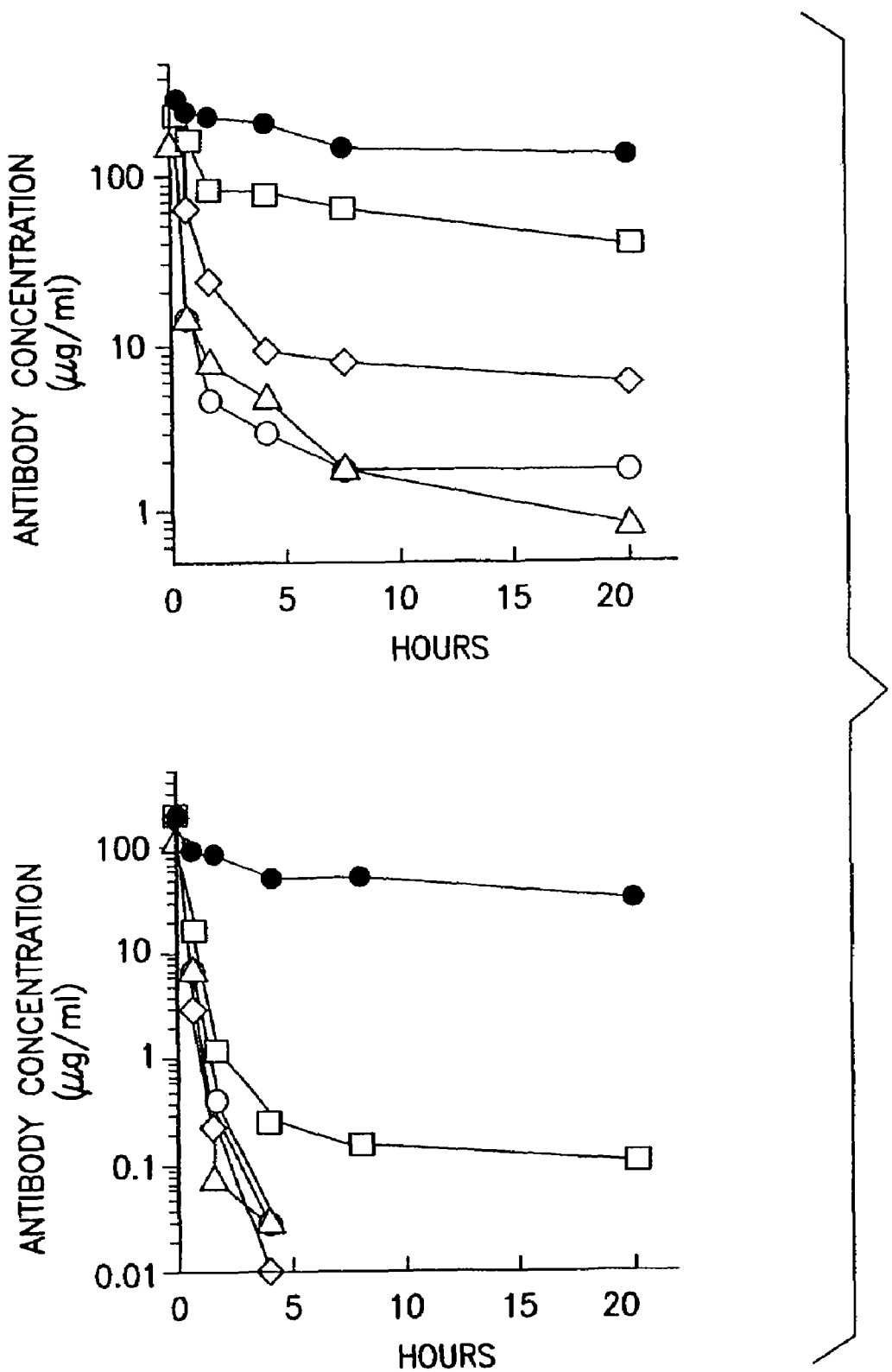
FIG. 8 shows the elimination of the galactose-modified antibodies from the serum of mice.

Antibodies against βG-PEG: Monoclonal antibodies against βG-sPEG were generated from spleen cells of mice that had received multiple injections of RH1-βG-PEG. mAb 1E8 (IgG$_1$) and AGP3 (IgM) were selected for further characterization based on preliminary screening by ELISA. The binding specificities of 1E8 and AGP3 are shown in FIGS. 1A and 1B. In FIG. 1A, 1E8 (squares) and AGP3

(circles) antibodies were incubated in microtiter plates coated with βG (open symbols) or βG-sPEG (filled symbols). In FIG. 1B, 1E8 (squares) and AGP3 (circles) were incubated in microtiter plates coated with BSA (open symbols) or BSA-sPEG (filled symbols). Binding of antibodies was detected by measuring the absorbance of the wells at 405 nm as described in the Experimental Procedures. The mean absorbance values of triplicate determinations are shown. Bars show the standard error of the mean. 1E8 bound to βG and, to a lesser extent, βG-sPEG (FIG. 1A). The apparent affinity constants of 1E8 for βG and BβG-sPEG were 0.83 and 1.8 nM, respectively (data not shown). In contrast, AGP3 bound βG-sPEG with an apparent affinity constant of 0.79 nM but did not bind βG (FIG. 1A), indicating that this antibody recognizes PEG chains present on βG-sPEG. AGP3 specificity for PEG was supported by the finding that it also bound BSA-sPEG but not BSA (FIG. 1B). As expected, 1E8 bound neither BSA nor BSA-sPEG (FIG. 1B). Neither of the mAbs affected the activity of βG (results not shown).

Figure 2:
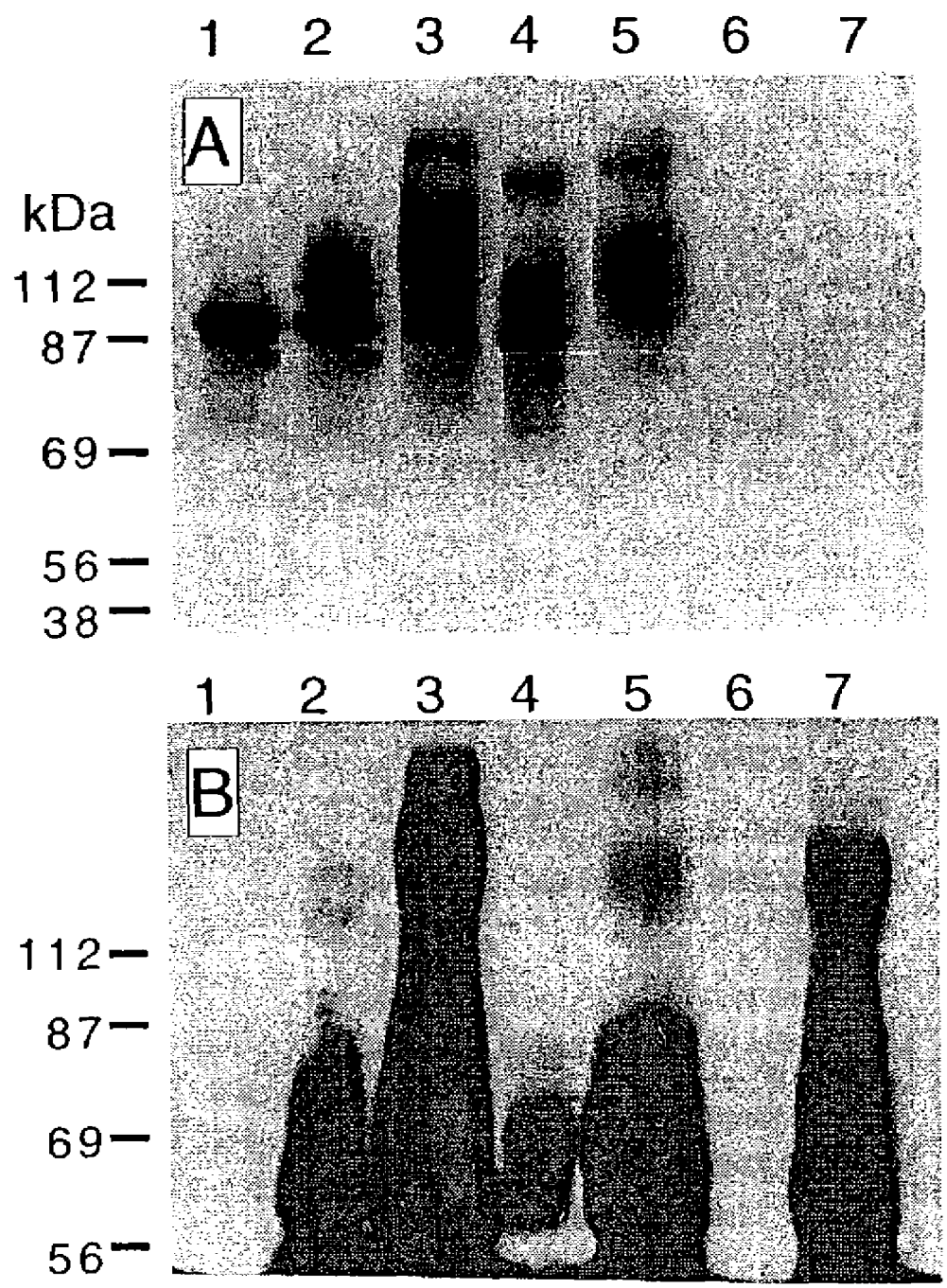
FIG. 2 is an immunoblot showing the binding of antibodies 1E8 and AGP3.

Specificity of the mAb binding was further examined by immunoblotting, as shown in FIGS. 2A and 2B. Proteins were electrophoresed in a 3-12.5% gradient reduced SDS-PAGE, transferred to nitrocellulose paper, and probed with 1E8 (2A) or AGP3 (2B) as described in the Experimental Procedures. Lane 1 is βG; lane 2 is βG-sPEG (2 mg of sPEG/mg of βG); lane 3 is βG-sPEG (20 mg of sPEG/mg of βG); lane 4 is βG-tPEG (2 mg of tPEG/mg of βG); lane 5 is βG-tPEG (20 mg of tPEG/mg of PG); lane 6 is BSA and lane 7 is BSA-sPEG. kDa represents molecular mass in thousands. The results show that 1E8 detected βG and PEG-modified βG (lanes 1-5), but not BSA or BSA-sPEG (lanes 6 and 7). FIG. 2B shows that AGP3, in contrast, did not bind βG (lane 1) or BSA (lane 6) but detected all proteins that incorporated PEG (βG-sPEG, βG-tPEG, and BSA-sPEG). The ability of AGP3 to bind either sPEG or tPEG-modified proteins demonstrates that this antibody binds to poly(ethylene glycol) rather that the linker between PEG and proteins.

Figure 3:
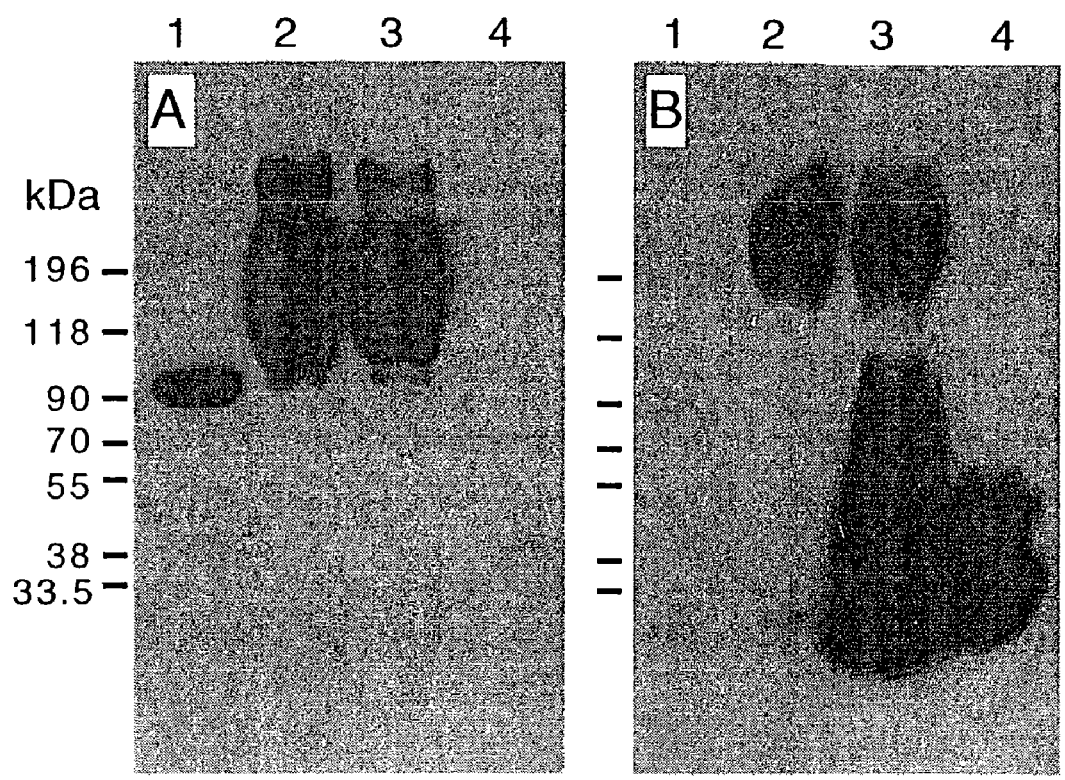
FIG. 3 is an immunoblot of different βG-PEG preparations.

FIGS. 3A and 3B demonstrate immunoblots of different βG-PEG preparations. Samples were electrophoresed on an 8% reduced SDS-PAGE, transferred to nitrocellulose paper, and probed with 1E8 (A) or AGP3 (B) as described in the Experimental Procedures. Lane 1 is βG; lane 2 is βG-sPEG purified by gel filtration; lane 3 is βG-sPEG purified by dialysis; and lane 4 is sPEG neutralized with excess glycine. kDa is molecular mass in thousands. Substantial amounts of free PEG were present in βG-sPEG preparations purified by dialysis (FIG. 3B, lane 3). AGP3 immunoblotting of sPEG after neutralization with glycine (FIG. 3B, lane 4) produced a similar smeared band, indicating that the low molecular weight material in βG-sPEG corresponded to free PEG rather than to degraded βG-sPEG fragments. Purification of βG-sPEG by gel filtration on Sephacryl S-200 HR resulted in the removal of free PEG (FIG. 3B, lane 2). This βG-PEG conjugate, containing 9.2±0.3 sPEG groups/βG subunit and possessing 69% of original enzymatic activity, was employed in all subsequent experiments using βG-sPEG.

Figure 4:
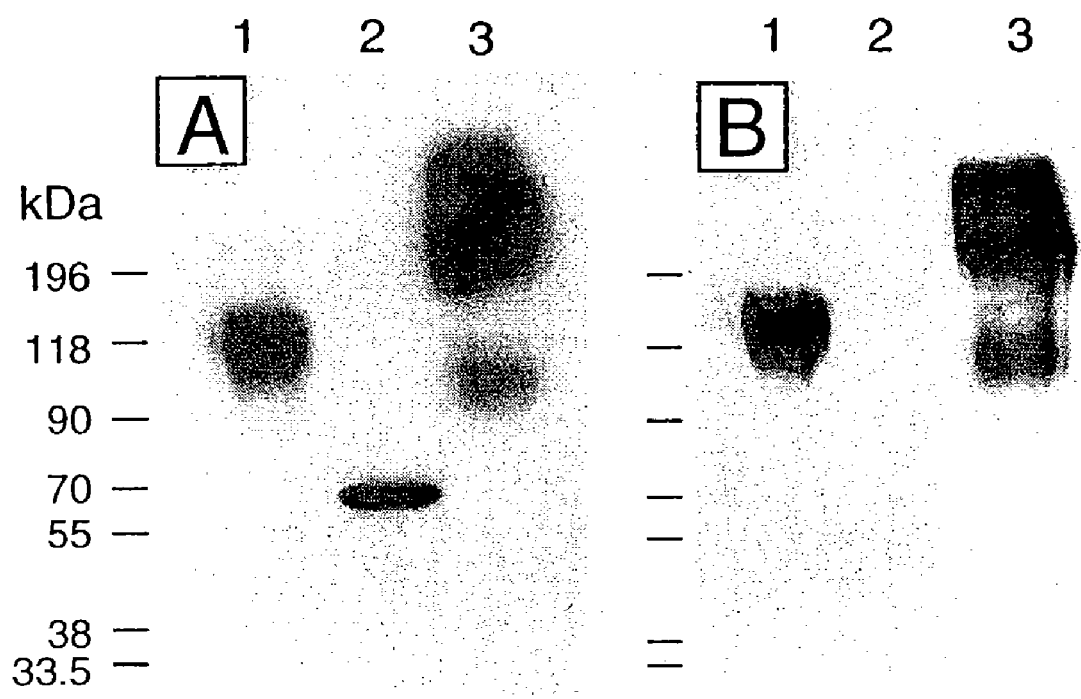
FIG. 4 is an immunoblot showing that AGP3 binds to the backbone of PEG rather than the linker or methoxy functions groups.

The antigen-binding specificity of AGP3 was further examined by immunoblotting, as shown in FIGS. 4A and 4B. Proteins were electrophoresed in a 3-12.5% polyacrylamide gel under reducing conditions, transferred to nitrocellulose paper and probed with mAb 1E8 (FIG. 4A) or AGP3 (FIG. 4B) as described in the Experimental Procedures. Lane 1 is βG-PEG-βG (βG modified with polyethylene glycol di-succinimidyl succinamide); lane 2 is unmodified βG; and lane 3 βG-pPEG (βG modified with methoxypolyethylene glycol succinimidyl propionate). The electrophoretic mobility of βG-pPEG (FIG. 4A, lane 3) was slower than unmodified βG (FIG. 4A, lane 2), demonstrating successful conjugation of pPEG to βG. βG was also successfully crosslinked with PEG to form βG-PEG-βG (FIG. 4A, lane 1). βG-PEG-βG does not contain a terminal methoxy group on the PEG chain. AGP3 bound βG-pPEG (FIG. 4B, lane 3) and βG-PEG-βG (FIG. 4B, lane 1) but not unmodified βG (FIG. 4B, lane 2). Binding of AGP3 to βG-PEG-βG shows that AGP3 binds to the backbone of PEG rather than the methoxy group present at the terminal of mPEG. This finding indicates that multiple AGP3 mAbs can bind to a single PEG chain and prompted us to examine whether AGP3 could be employed in a sandwich ELISA for the detection of PEG-modified proteins.

Figure 5:
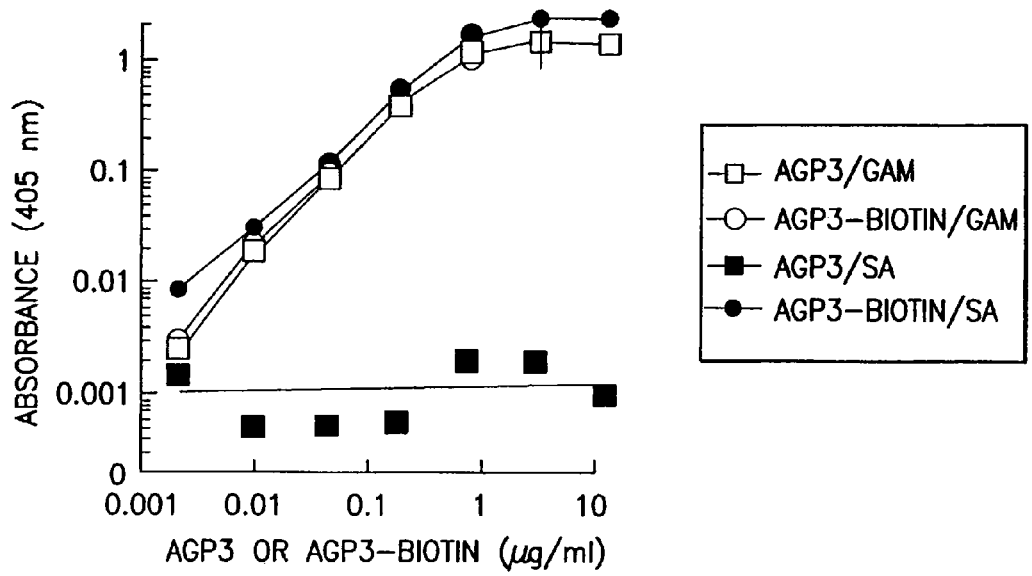
FIG. 5 shows the activity of biotin-labeled AGP3.

AGP3 ELISA: AGP3 was examined for use in the ELISA detection of PEG-modified proteins. AGP3 was modified with a 25-fold molar excess of NHS-LC-biotin to produce AGP3-biotin. In FIG. 5, AGP3 (squares) or AGP3-biotin (circles) were incubated in a microtiter plate coated with βG-tPEG. Antibody binding to immobilized PEG was detected with HRP-GAM μ-chain antibody (open symbols) or streptavidin-HRP (filled symbols). Results represent average values of duplicate determinations. AGP3-biotin retained the same antigen binding activity to βG-tPEG as AGP3 in ELISA using HRP-GAM μ-chain antibody for detection (FIG. 5). Detection of antibody binding to βG-PEG with streptavidin-HRP showed that AGP3-biotin but not AGP3 could be detected (FIG. 5), demonstrating that biotin was indeed incorporated into AGP3-biotin.

Figure 6:
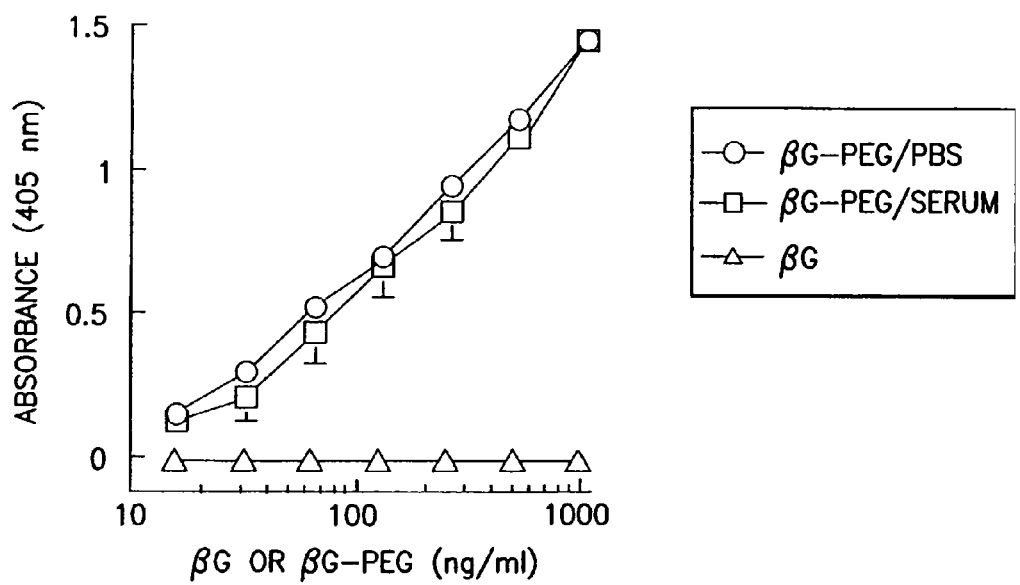
FIG. 6 shows measurement of PEG-modified protein by AGP3 ELISA.
Figure 7:
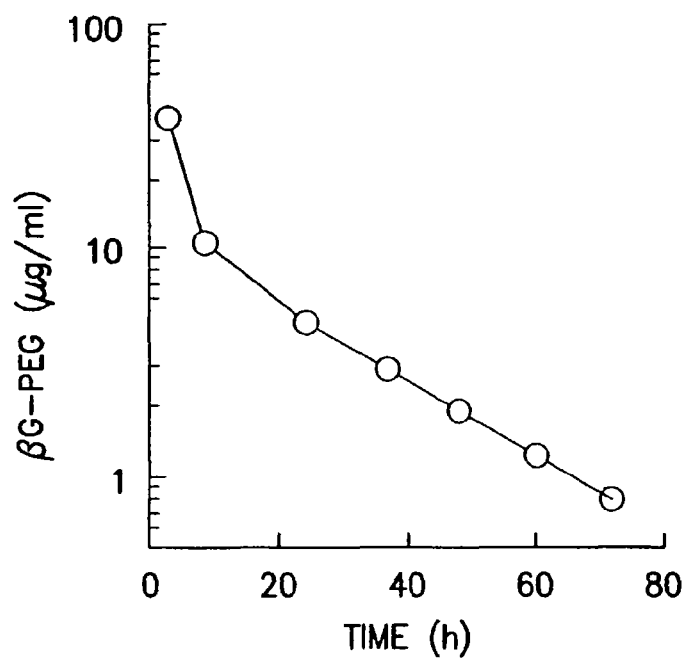
FIG. 7 shows measurement of βG-PEG pharmacokinetics by AGP3 ELISA.

A sandwich ELISA was developed in which AGP3 was employed for the capture step and AGP3-biotin used for detection. In FIG. 6, serial dilutions of βG-pPEG in PBS (○) or 10% mouse serum (□) as well as βG in PBS (Δ) were incubated in a microtiter plate coated with AGP3. Binding of βG-pPEG to the immobilized AGP3 was detected by sequential addition of AGP3-biotin and streptavidin-HRP. Results represent mean values of triplicate determinations. Bars indicate the standard error of the mean. FIG. 6 shows that this assay could detect βG-pPEG at concentrations at least as low as. 15 ng/ml. This corresponds to 2.6 fmol of βG-pPEG or 500 pg of PEG. The assay only detected PEG-modified protein as shown by the lack of signal when unmodified βG was assayed (FIG. 6). The effect of serum on the ELISA was examined by adding 10% mouse serum to samples before assay. The sensitivity of the assay was about the same as without serum (FIG. 6), indicating that this ELISA should be applicable to pharmacokinetic studies of PEG-modified molecules and proteins. The AGP3 ELISA was employed to measure the pharmacokinetics of βG-pPEG in mice. In FIG. 7, a BALB/c mouse was i.v. injected with 150 μg βG-pPEG. Blood samples were periodically removed from the tail vein and assayed for βG-pPEG concentration by ELISA. FIG. 7 shows that after a period of rapid clearance, βG-pPEG was eliminated from the circulation with a first-order half-life of 19.2 h. This result indicates that the newly developed ELISA can be employed to determine the pharmacokinetics of PEG-modified compounds.

There are currently no methods to directly measure low concentrations of intact PEG-conjugates for pharmacological studies. Conjugates can be indirectly measured by first radiolabeling the protein (Kaneda et al., 1995; Cheng et al., 1997; Yabe et al., 1999) or PEG (Mullin et al., 1997), but radioisotopes pose safety concerns and require special handling. Functional assays can be employed to measure the concentration of the protein component of conjugates (Esslinger et al., 1997; Cheng et al., 1999), but no information is provided about the stability of covalently attached PEG chains. Methods that measure the number of PEG molecules attached to a protein (Habeeb, 1966; Stocks et al., 1986) require that purified conjugate be employed which is difficult to achieve in pharmacokinetic studies. Methods that directly measure the concentration of PEG are relatively insensitive. Colorimetric methods based on complex formation between barium-iodide and PEG require that proteins are first removed and have detection limits of around 1-5 µg PEG (Childs, 1975). A calorimetric method based on partitioning of a chromophore present in aqueous ammonium ferrothiocyanate reagent can be employed for complex protein mixtures but has a detection limit of 1-5 µg PEG (Nag et al., 1996; Nag et al., 1997). High performance liquid chromatography can measure PEG with a detection limit around 1-5 µg/ml (Kinahan and Smyth, 1991; Ryan et al., 1992; Ruddy and Hadzija, 1994; Miles et al., 1997). Phase-partitioning can be employed to measure PEG but the assay sensitivity is about 1 µg PEG (Guermant et al., 1995). Finally, polyclonal antibodies against PEG can detect the presence of 1 µg/ml PEG in PEG-modified proteins (Richter and Akerblom, 1983). The newly developed ELISA can measure 500 pg of PEG in βG-pPEG, approximately 4 orders of magnitude more sensitive than other methods. In addition, the AGP3 ELISA does not require prior separation of PEG-conjugates from complex mixtures, simplifying application to pharmacokinetic studies.

Glactose-Modification of Antibodies: 1E8 and AGP3 were derivatized with galactose to target their uptake by the asialoglycoprotein receptor on hepatocytes. Modification of 1E8 with increasing amounts of activated galactose resulted in the incorporation of up to 47 galactose residues/antibody, as shown in Table 1.

with a 2.4-fold decrease in antigen-binding activity at the highest levels of galactose incorporation.

The half-lives of galactose-modified antibodies were determined in BALB/c mice, as shown in FIGS. 8A and 8B. Each of the BALB/c mice was i.v. injected with 200 µg of 1E8 (●), 1E8-9G (□), 1E8-19G (◇), 1E8-36G (Δ), or 1E8-46 (○) (FIG. 8A) or 200 µg of AGP3 (●), AGP3-64G (□), AGP3-130G (◇), AGP3-208G (Δ), or AGP3-285G (○) (FIG. 8B). The concentration of antibodies in serum samples taken at the indicated times was measured as described in the Experimental Procedures. FIG. 8A shows that 1E8 was eliminated from serum with a half-life of 22 h. Introduction of increasing numbers of galactose residues into 1E8 resulted in progressively faster initial clearance rates. Even at the highest galactose incorporation, however, residual concentrations of 14 µg/mL 1E8-46G were present in the serum after 5 h. Unmodified AGP3 cleared from serum with a half-life of 13 h but in contrast to galactose-modified 1E8, almost no residual antibody could be detected in the circulation within 5 h after administration of AGP3 modified with more than 130 galactose moieties (FIG. 8B). Increasing the level of galactose residues per antibody did not greatly affect the initial rate of clearance, but did increase the total amount of antibody that was removed from the circulation. For example, the concentrations of 1E8-9G, 1E8-19G and 1E8-36G in serum were 45%, 5.3% and 1.2% of 1-E8 levels after 8 h. The galactose-modified antibodies that were not removed from the circulation within the first 5 h exhibited similar elimination kinetics as unmodified 1E8, indicating that a critical number of galactose residues was required for efficient uptake by the asialoglycoprotein receptor, similar to the results found for galactosylated BSA and superoxide dismutase (Nishikawa et al., 1995). The more efficient uptake of galactosylated AGP3 (99.5% by 4 h for ≥130

TABLE 1

Characteristics of Galactose-Modified Monoclonal Antibodies

| Galatose added[a] | Conjugate | Incorporated galactose Groups/mAb Fluor[b] | Activity[d] | Conjugate | Incorporated-galactose Gropup/mAb | | Activity[d] |
|---|---|---|---|---|---|---|---|
| (mg/mg) | Name | TNBS[c] | (% control) | Name | Flour[b] | TNBS[c] | (% control) |
| 0 | 1E8 | 0 | 0 | 100 | AGP3 | 0 | 0 | 100 |
| 0.9 | 1E8-9G | 12 ± 0 | | 100 | AGP3-64G | 60 ± 18 | 67 ± 10 | 72 |
| 1.8 | 1E8-19G | 7 ± 0.6 | | 82 | AGP3-130G | 130 ± 4 | 130 ± 13 | 64 |
| 5.5 | 1E8-36G | 17 ± 2 | | 72 | AGP3-208G | 210 ± 8 | 205 ± 21 | 48 |
| 10.9 | 1E8-46G | 21 ± 2 | | 62 | AGP3-285G | 290 ± 0.1 | 280 ± 8 | 43 |
| 16.4 | 1E8-47G | 35 ± 07 | | 66 | AGP3-295G | 310 ± 0.1 | 280 ± 7 | 42 |
| | | 37 ± 2 | | | | | | |
| | | 48 ± 01 | | | | | | |
| | | 44 ± 3 | | | | | | |
| | | 47 ± 0.3 | | | | | | |
| | | 46 ± 2 | | | | | | |

[a]The amount of activated galactose added per milligram of antibody.
[b]Determined by the fluorescamine method as described by Stocks et al. (1986).
[c]Determined by the trinitrobenzesulfonic acid method as described in the Experimental Procedures,
[d]Antigen-binding activity determined by ELISA.

Introduction of up to 20 galactose residues did not affect the binding of 1E8 to βG whereas greater incorporation of galactose decreased 1E8 activity by about 35%. A maximum of about 290 galactose residues could be introduced into AGP3 (Table 1). The greater number of galactose residues incorporated into AGP3 primarily reflects the larger size of the IgM molecule; galactose incorporation for both 1E8 and AGP3 corresponded to 0.3 galactose moieties/kDa of antibody. AGP3 was more sensitive to galactose modification galactose moieties) compared to galactose-modified 1E8 was unlikely due to differences in the surface density of galactose groups since galactose incorporation was similar based on the molecular weights of 1E8 and AGP3. The asialoglycoprotein receptor is a hetero-oligomer composed of two types of polypeptide chains (Lodish, 1991). High affinity binding of ligands involves the-interaction of three galactose residues in ligands with sites in both polypeptide chains (Rice et al., 1990). Specific orientation of the galactose residues is required for high affinity receptor binding (Lee et al., 1983; Townsend et al., 1986), suggesting that the orientation of incorporated galactose groups in the pentameric structure of IgM may promote high-affinity binding to the asialoglycoprotein receptor. On the basis of the elimination kinetics of the antibodies, 1E8-36G and AGP3-208G were selected for further study.

Figure 9:
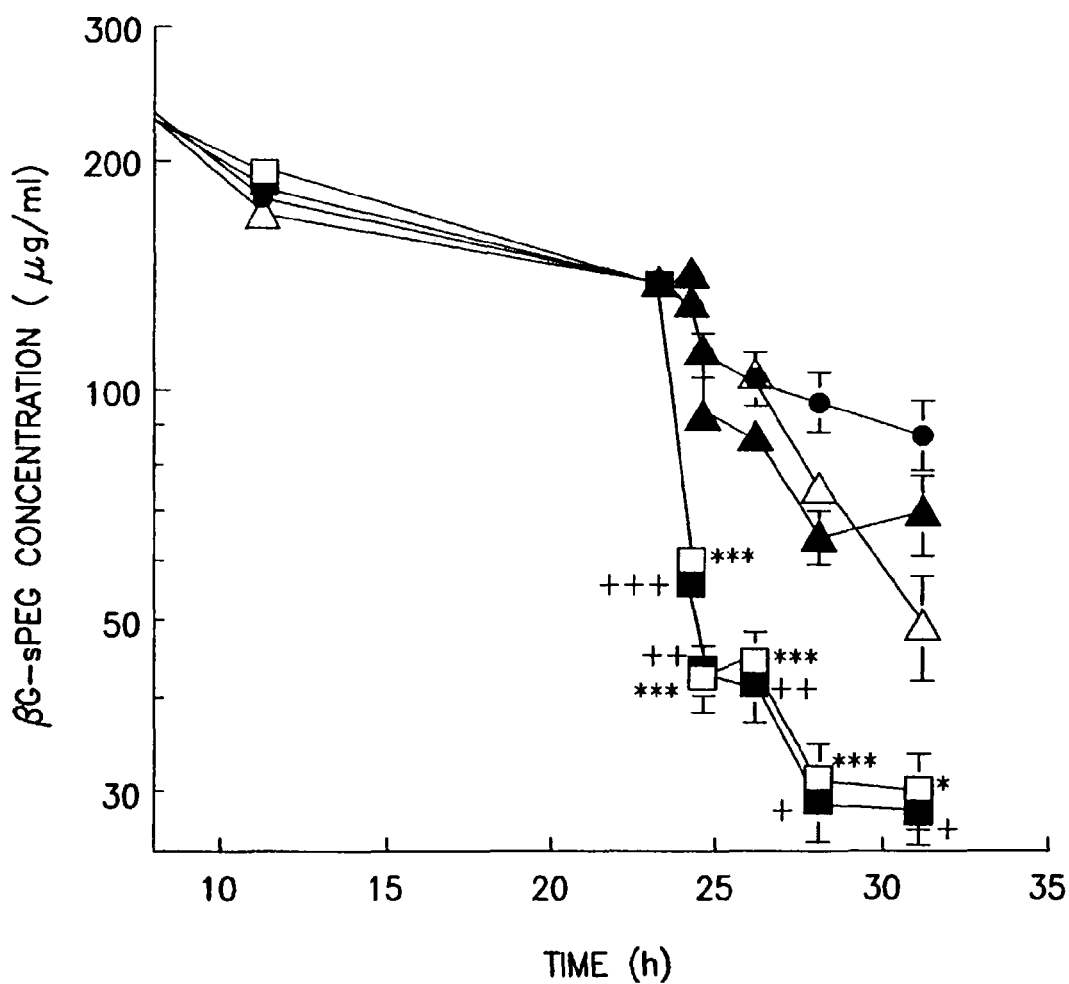
FIG. 9 shows the clearance of βG-PEG by antibodies.

In vivo Clearance of βG-PEG: The ability of mAbs 1E8 and AGP3 to clear βG-sPEG from the circulation is shown in FIG. 9. Mice injected with 200 μg of βG-sPEG at time 0 were i.v. injected 23 h later with PBS ( ) or 250 μg of 1E8 (Δ), 1E8-36G (▲), AGP3 (□), or AGP3-208G (■). The concentration of βG-sPEG in serum samples was measured and normalized as described in the Experimental Procedures. Mean concentrations from three mice are shown. Significant differences between AGP3 and 1E8 clearance are indicated by: *, $p \leq 0.05$; , $p \leq 0.005$; *, $p \leq 0.0005$. Significant differences between 1E8-36G and AGP3-208G clearance are indicated by: +, $p \leq 0.05$; ++, $p \leq 0.005$; +++, $p \leq 0.0005$. Bars indicate the standard error of the mean. As shown in FIG. 9, both 1E8 and AGP3 accelerated the clearance of βG-sPEG from the circulation. 1E8-36G cleared significantly more βG-sPEG than 1E8 at early times but by 8 h after antibody administration there was no significant difference between these antibodies. AGP3 and AGP3-208G cleared significantly more βG-sPEG than either 1E8 or 1E8-36G at all times examined. βG-sPEG was cleared equally well by AGP3 and AGP3-208G under these experimental conditions.

Figure 10:
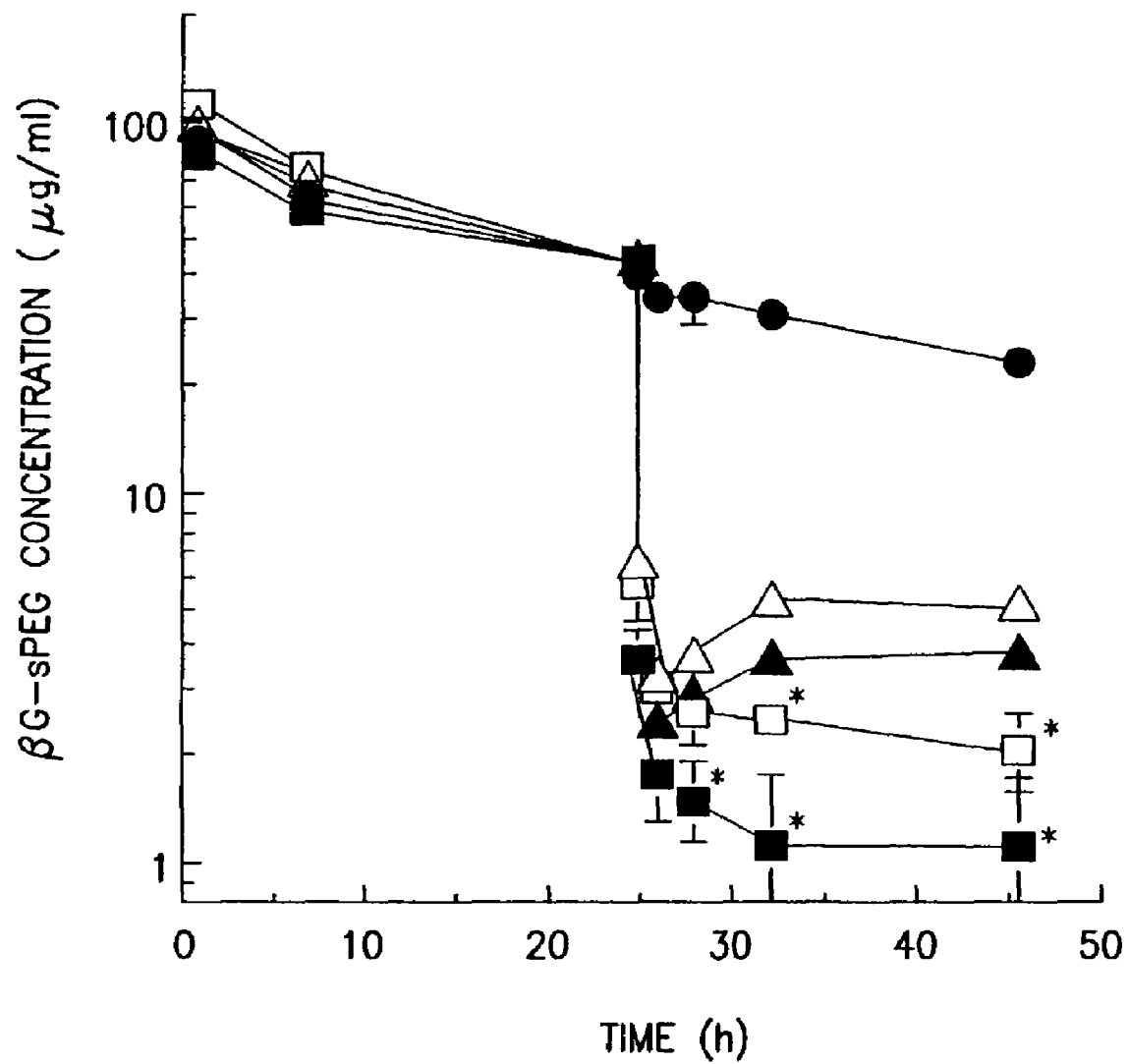
FIG. 10 shows the dose dependency of the clearance of βG-PEG by AGP3.

FIG. 10 shows a dose dependent relation between AGP3 dose and efficiency of βG-sPEG clearance. Groups of three mice were injected at time 0 with 50 μg of βG-sPEG followed 24 h later by PBS (●), 150 μg of AGP3 (□), 150 μg of AGP3-208G (Δ), 300 μg of AGP3 (■), or 300 μg of AGP3-208G (▲). The concentration of βG-PEG in serum samples was measured and normalized as described in the Experimental Procedures. Mean concentrations from three mice are shown. Significant differences between AGP3 and AGP3-208G groups are indicated by; *, $p \leq 0.05$. Bars indicate the standard error of the mean. FIG. 10 shows that i.v. injection of 150 or 300 μg of AGP3 or AGP3-208G 24 h after i.v. injection of 50 μg of βG-sPEG resulted in rapid removal of 90-95% of the enzyme within 1.5 h. The concentration of βG-sPEG in the circulation, however, rebounded from a minimum of about 2 μg/mL to 4-5 μg/mL 8 h after injection of AGP3-208G. In contrast, the concentration of βG-sPEG decreased to 1.0 μg/mL 8 h after injection of 300 μg of AGP3. Although a dose of 300 μg of AGP3 appeared to more completely clear βG-sPEG compared to 150 μg of AGP3, the difference was only significant $p \leq 0.05$) 1.5 h after antibody administration. In contrast, clearance of βG-sPEG with both 150 and 300 μg of AGP3 was significantly ($p \leq 0.05$) better than clearance with either dose of AGP3-208G at all times. The better clearance achieved by unmodified AGP3 can be attributed to the prolonged half-life of AGP3 ($\tau_{1/2}$=13 h) compared to AGP3-208G ($\tau_{1/2}$<1 h). βG-sPEG released from normal tissues after rapid removal from blood could be bound and cleared by free AGP3 remaining in the blood pool whereas the rapid endocytosis of both free and complexed AGP3-208G prevented further formation of complexes with βG-sPEG. This behavior is clearly evident in FIG. 10 where the concentration of βG-sPEG in the circulation rebounded after an initial period of rapid clearance by AGP3-208G. AGP3 also efficiently cleared 5A8-βG-PEG, reducing the serum concentration of conjugate by 280 fold within 2 hours and by 940 fold within 48 hours, as shown in Table 2.

Hindered binding of 1E8 by PEG chains on βG-sPEG may have contributed to the high residual serum concentrations of βG-sPEG after 1E8 administration. The pentameric structure of AGP3 combined with the presence of multiple PEG chains on each βG tetramer may have promoted the formation of large immune complexes, which are cleared more rapidly than small immune complexes. AGP3 appears to produce more rapid and complete clearance than other antibodies previously employed for clearance, which have been limited to IgG fractions of polyclonal antiserum (Bradwell et al., 1983; Sharkey et al., 1984; Begent et al., 1989; Pedley et al., 1989) or monoclonal IgG antibodies (Sharma et al., 1990; Kerr et al., 1993; Haisma et al., 1995). Polyclonal IgG antibodies reduced radioimmunoconjugate levels in serum from around 10-fold (Bradwell et al., 1983; Sharkey et al., 1984; Begent et al., 1989) to 130-fold (Pedley et al., 1989) in 24 h whereas monoclonal IgG antibodies reduced the serum levels of antibody-enzyme conjugates from 3-10 fold in a few hours (Sharma et al., 1990; Haisma et al., 1995) to 40-60 fold in 24 h (Kerr et al., 1993; Wallace et al., 1994). In comparison, AGP3 reduced the serum concentration of 5A8-βG-PEG by 280-fold in 2 h and 940-fold in 24 h. Although it is difficult to directly compare clearance results employing different immunoconjugates and experimental conditions, these results suggest that IgM may clear immunoconjugates from blood more rapidly and completely than IgG.

TABLE 2

| | Clearance of 5A8-βG-PEG by AGP3 | | |
|---|---|---|---|
| Time | No clearance | AGP3 clearance | |
| (hour) | (μg/mL) | (μg/mL) | reduction[b] (fold) |
| 24 | 24 ± 2.1 | 37 ± 1.5 | 1.0 |
| 26 | 18 ± 3.5 | 0.10 ± 0.001 | 280 |
| 48 | 6.1 ± 0.7 | 0.01 ± 0 | 940 |

[a]Groups of 3 mice were i.v. injected with 175 μg of 5A8-βG-PEG. At 24 and 25 hours, mice were injected with PBS (no clearance) or 300 μg of AGP3. The concentration of 5A8-βG-PEG in serum was determined by measuring βG activity.
[b]The ratio of 5A8-βG-PEG in serum without clearance to the concentration with clearance, normalized for the difference in conjugate concentrations at 24 hour.

PEG modification is a useful technique to improve the stability, prolong serum half-life and decrease the antigenicity and immunogenicity of proteins. Since AGP3 binding to PEG is protein independent, this antibody may be generally applicable to clearance of any PEG-modified immunoconjugates. However, clearance of immunoconjugates from the circulation may also result in decreased tumor accumulation of the immunoconjugates, probably due to a concentration gradient of the conjugates from tumor to blood, which allows the immuconjgates to be dissociated from tumor antigen and released into the blood. But this undesirable process may be slowed down by using IgM type antibodies since IgM is larger in size, which may delay its entrance into the tumor interstitial space thereby minimizing interactions between localized immunoconjugates and the antibody. In addition, the rapid clearance achieved by using AGP3 permits administration of prodrugs or other targets before a significant amount of immunoconjugates are released from the tumor.

Figure 11:
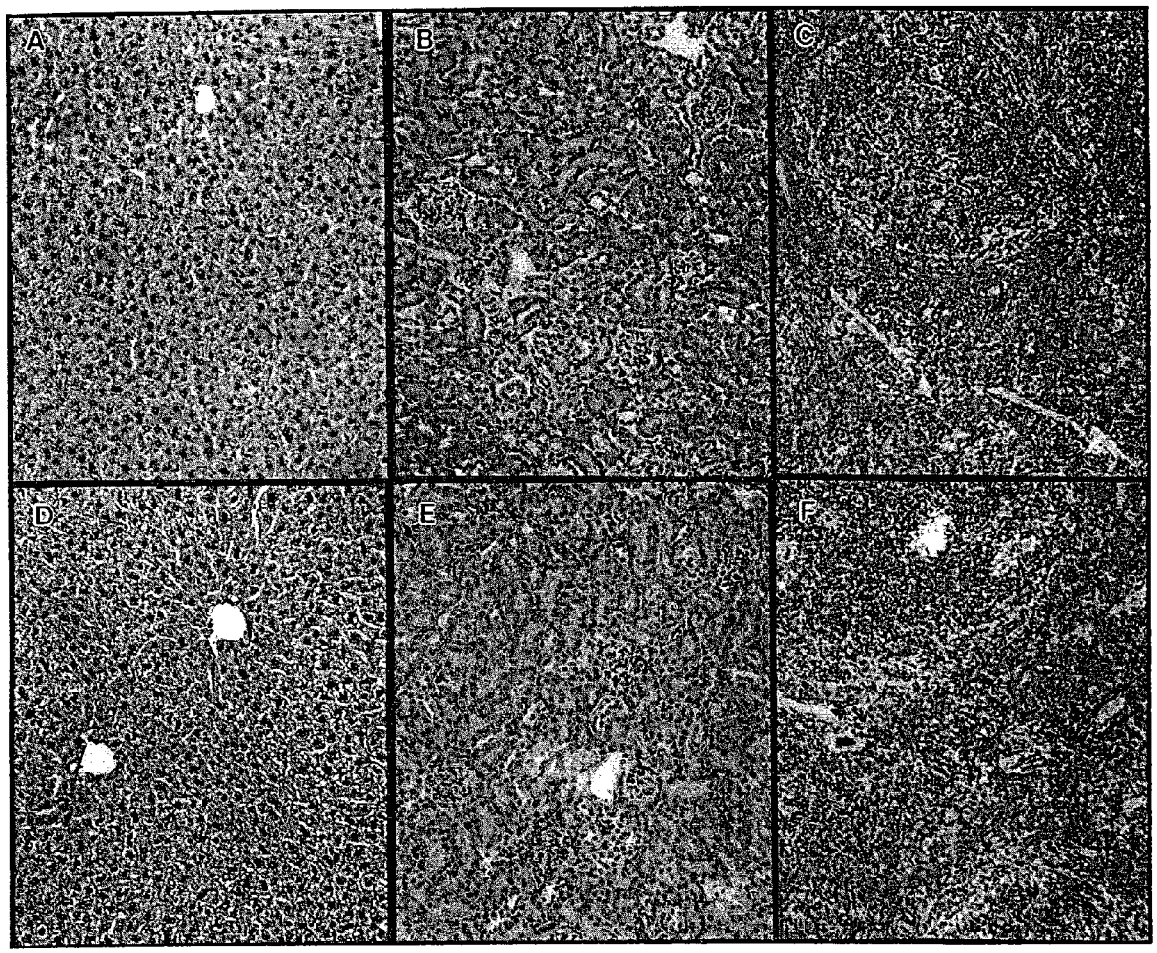
FIG. 11 shows the BHAMG-induced organ pathology after βG-PEG clearance.

Prodrug Toxicity after Clearance of βG-sPEG: Clearance of circulating βG-sPEG should reduce systemic activation of the glucuronide prodrug BHAMG, thereby reducing toxicity. One concern of employing IgM to clear proteins is that the immune complexes could be deposited in organs and cause tissue damage. In addition, deposition of βG-PEG on the surface of cells could result in prodrug activation and tissue toxicity. Organ tissue sections from mice that were injected with PBS or βG-sPEG followed 24 h later by AGP3 and then BHAMG were examined after 3 or 10 days as shown in FIG. 11. Mice were injected with PBS (A-C) or βG-sPEG (D-F) on day 1. Mice were i.v. injected with AGP3 and with BHAMG 24 and 30 h later, respectively. Tissue sections of liver (A, D), kidney (B, E), and spleen (C, F) recovered 10 days later were stained with hematoxylin and eosin. FIG. 11 shows that the injection of AGP3 and BHAMG as well as clearance of βG-sPEG with AGP3 before BHAMG administration did not cause obvious damage to the liver, spleen, or kidney 10 days after BHAMG administration. Similarly, no tissue damage was observed 3 days after prodrug administration (results not shown).

Figure 12:
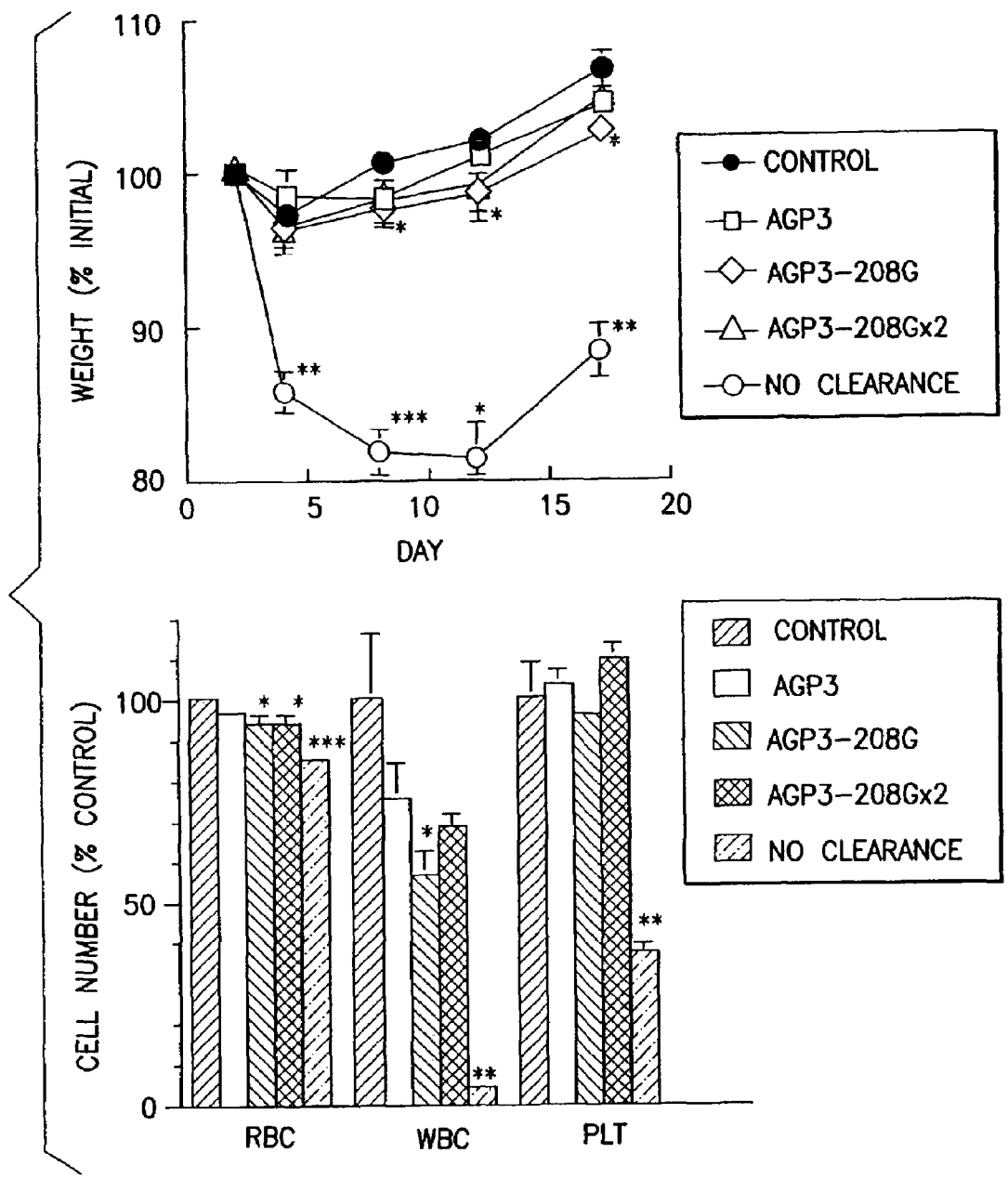
FIG. 12 shows the weight changes of the mice and hematological toxicity of BHAMG after the clearance of βG-PEG.

The toxicity associated with clearance and prodrug administration was also assessed by measuring the weight and blood cells of mice, as shown in FIGS. 12A and 12B. Groups of 4 mice were i.v. injected at time zero with PBS (control) or βG-sPEG. Twenty-four hours later, mice received i.v. injections of 300 μg of AGP3 (control and AGP3 groups), 300 μg of AGP3-208G, 150 μg of AGP3-208G (×2, 4 h delay), or PBS (no clearance). Six hours later, all mice were i.v. injected with BHAMG. FIG. 12A shows the time course of mouse weight (% of initial weight) and FIG. 12B shows the mean numbers of WBC, RBC, and platelets on day 8. Significant differences between the control and experimental groups are indicated by: *, $p \leq 0.05$; , $p \leq 0.005$; *, $p \leq 0.0005$. Bars indicate the standard error of the mean. Administration of AGP3 and 15 mg/kg BHAMG (control group) produced only a small transient decrease in the weight of mice (FIG. 12A). In contrast, injection of 50 μg of βG-sPEG 24 h before administration of BHAMG (no clearance) caused significant weight loss and resulted in the death of 1 of 4 mice. Clearance of βG-sPEG with 300 μg of AGP3 or 2 injection of 150 μg of AGP3-208G before prodrug administration prevented significant weight loss compared to the control group. Mice that were cleared with one 300 μg dose of AGP3-208G before injection of BHAMG lost significantly more weight than control mice after day 8, but the loss was much less than in the uncleared mice. FIG. 12B shows that the numbers of RBC, WBC and PLT were significantly reduced in mice injected with βG-sPEG and BH-AMG (no clearance) compared to mice injected with AGP3 and BHAMG (control mice). In contrast, the numbers of RBC, WBC, and PLT in mice in which βG-sPEG was cleared with 300 μg of AGP3 before BHAMG administration were not significantly different from control mice. Clearance of βG-sPEG with AGP3-208G before injection of prodrug reduced but did not eliminate hematological toxicity.

Figure 13:
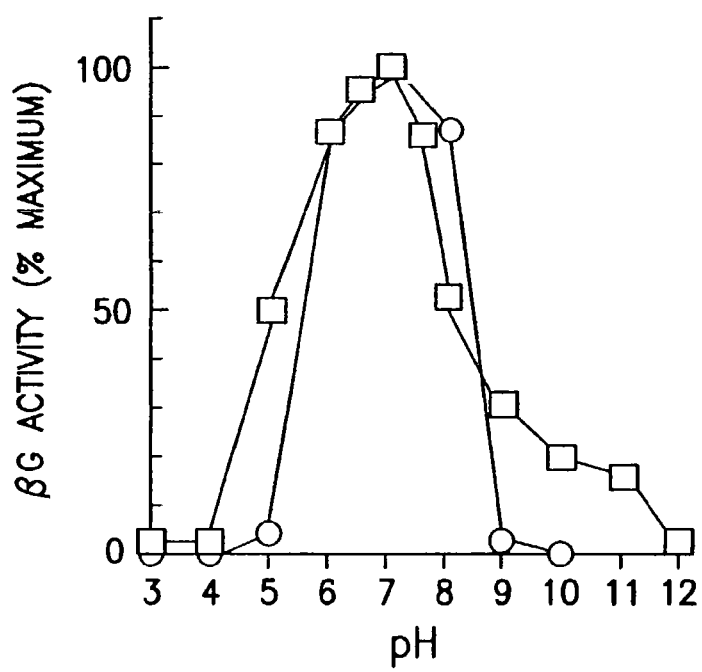
FIG. 13 shows the pH sensitivity of βG.

AGP3/βG-PEG immune complexes may be routed to the acidic environment of lysosomes after clearance. The pH sensitivity of βG is shown in FIG. 13. βG was assayed for enzymatic activity at various pH values (□) or incubated at the indicated pH for 4 h before neutralization and assay at pH 7.0 (○). Results represent percentage of maximum activity. βG was irreversibly deactivated at pH values less than 5.0 or greater than 9.0 (FIG. 13).

Soluble IgM immune complexes are primarily removed from the circulation and catabolized by the mononuclear phagocyte system in the liver, spleen and lungs, possibly by receptor-mediated binding of high mannose oligosaccharides exposed upon conformational changes in IgM after binding to antigen (Day et al., 1980). The low toxicity of BHAMG after clearance of βG-sPEG with AGP3 indicates that immune complexes formed between AGP3 and βG-sPEG are rapidly internalized where βG is inactivated, degraded or inaccessible to prodrug. Routing of βG-sPEG to lysosomes is expected to result in loss of enzymatic activity because βG is irreversibly inactivated at pH values lower than 5.0. Deactivation of βG in lysosomes may prevent accumulation of active enzyme and prodrug activation in the liver as observed after antibody-mediated clearance of carboxypeptidase G2 conjugates (Rogers et al., 1995).

Figure 14:
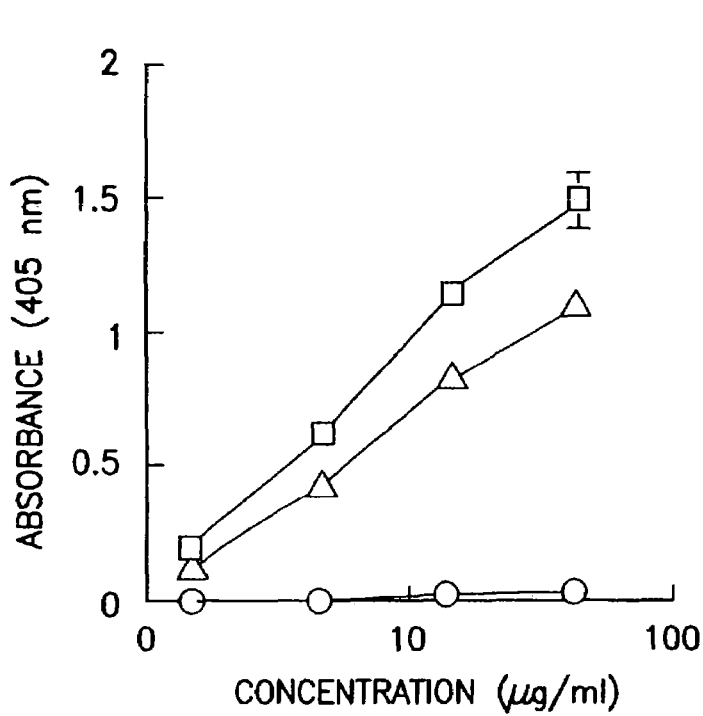
FIG. 14 shows the activity of B72.3-βG-PEG and H25-βG-PEG.
Figure 14:
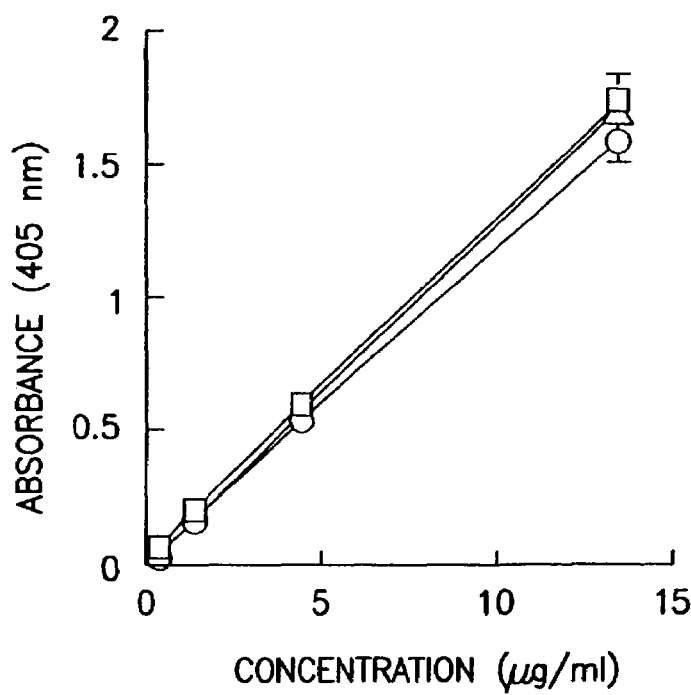

Characterization of the LS174T tumor model: LS174T colon adenocarcinoma cells were used as a human tumor model to examine the effect of clearance on the localization and therapeutic efficacy of glucuronide prodrug activation by B72.3-βG-PEG, a conjugate formed by covalently linking F(ab')₂ fragments of mAb B72.3 to PEG-modified βG. In FIG. 14A, mAb B72.3 (□), B72.3-βG-PEG (Δ) and the control conjugate H25-βG-PEG (○) were assayed by ELISA for binding to bovine submaxillary gland mucin. Absorbance (405 nm) of wells was measured 30 min after addition of ABTS. substrate. In FIG. 14B, the absorbance (405 nm) of wells containing the indicated concentrations of βG (□), B72.3-βG-PEG (Δ) and H25-βG-PEG (○) was measured 15 min after addition of PNPG substrate. Results show the mean values of duplicate determinations. Bars indicate the standard error of the mean. B72.3-βG-PEG retained 75% of the mucin binding activity of mAb B72.3 (FIG. 14A) and 100% of the enzyme activity of unmodified βG (FIG. 14B). Control conjugate H25-βG-PEG did not bind LS174T cells (FIG. 14A) but retained 92.4% of native βG activity (FIG. 14B).

Figure 16:
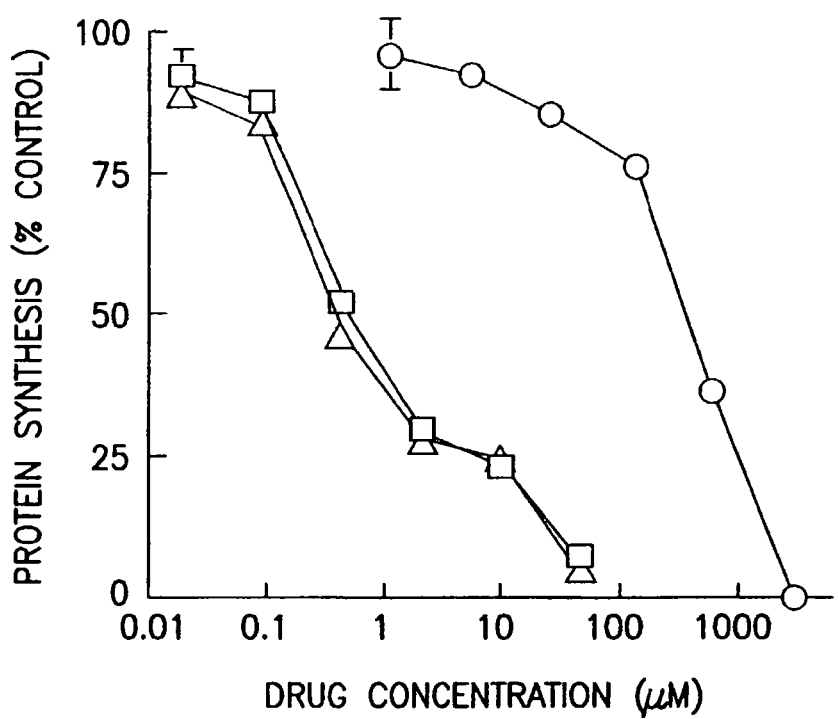
FIG. 16 shows the sensitivity of LS174T tumor cells to pHAM and BHAMG.
Figure 15:
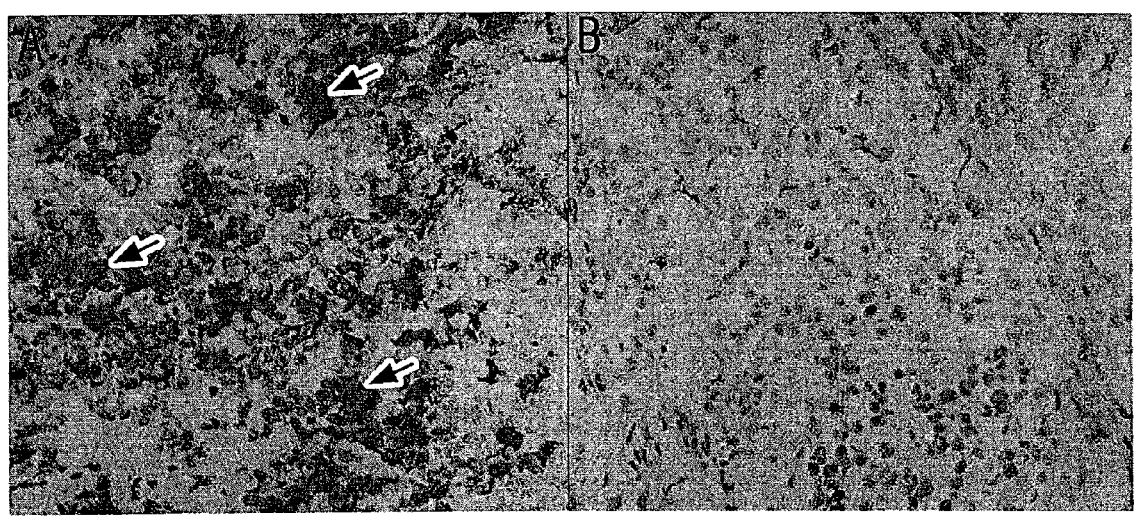
FIG. 15 shows the specificity of mAb B72.3 to LS174T xenografts.

As shown in FIG. 15, frozen section of LS174T tumors were incubated with mAb B72.3 (A) or H25B10 (B) followed by biotin-labeled goat anti-mouse Ig and streptavidin-HRP before addition of substrate. Magnification is 200×. The sections were counterstained with hematoxylin. Examples of positive immunostaining are indicated with arrows. Immunohistochemical analysis of antibody binding confirmed that mAb B72.3 (FIG. 15A) but not mAb H25B10 (FIG. 15B) bound to LS174T xenografts. mAb B72.3 binding to LS174T sections was heterogeneous (FIG. 15A). The sensitivity of LS174T tumor cells to pHAM and BHAMG was determined by measuring [³H]-leucine incorporation into cellular proteins after exposure to drugs for 24 h. Comparison of $IC_{50}$ values showed that BHAMG was 800 times less toxic than pHAM to LS174T cells as shown in FIG. 16 where LS174T colon adenocarcinoma cells were exposed to pHAM (□), BHAMG (○) or BHAMG plus 1 μg/well βG (Δ) for 24 h, washed with PBS and incubated in fresh medium for 24 h before [³H]-leucine incorporation was determined. The cellular protein synthesis rate of drug-treated cells is compared to untreated control cells. Bars indicate the standard error of triplicate determinations. The simultaneous addition of βG and BHAMG to tumor cells resulted in a cytotoxic effect equal to pHAM alone, indicating efficient cleavage of the glucuronide functional group of BHAMG.

Figure 17:
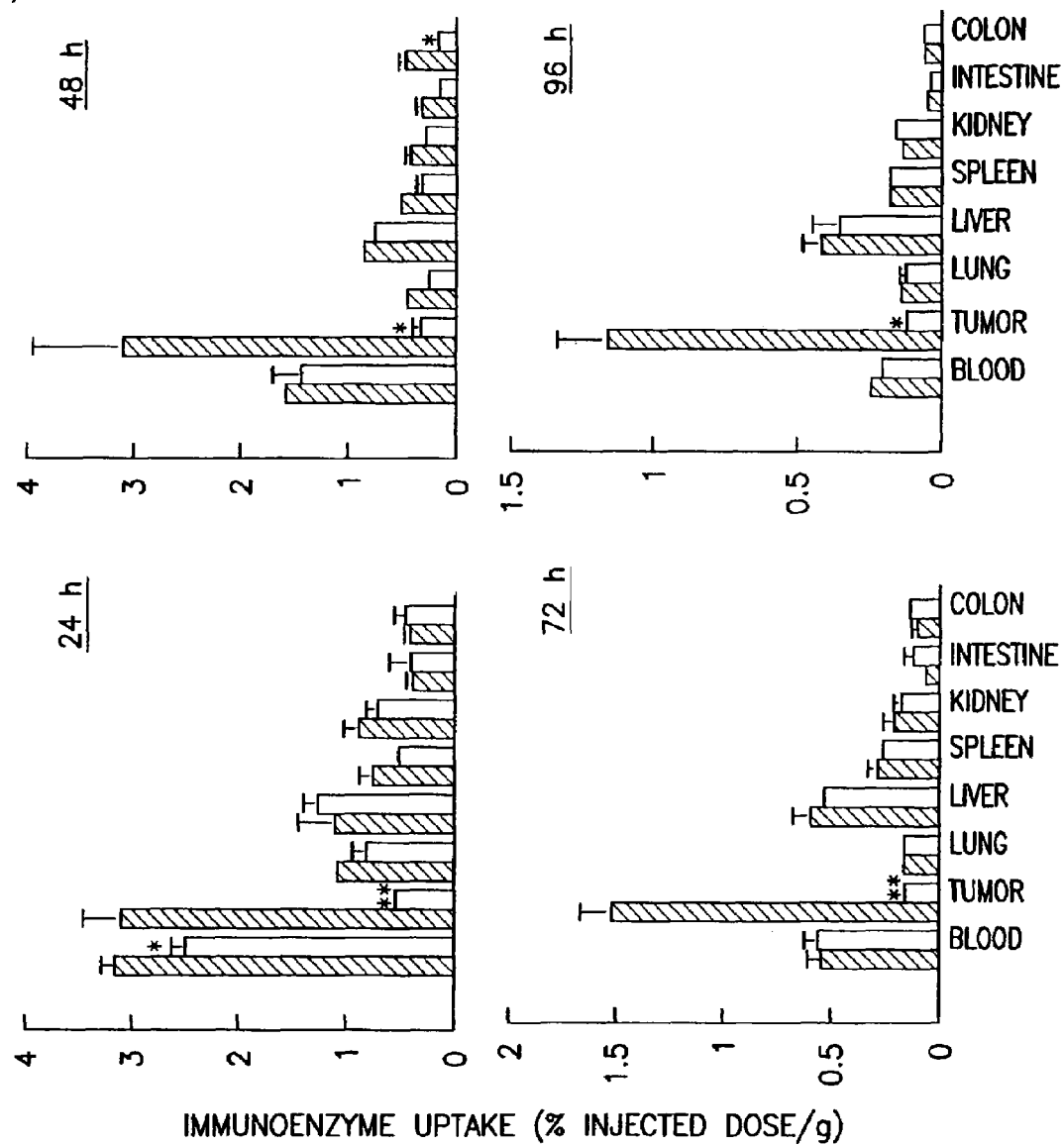
FIG. 17 shows the biodistribution of [$^{125}$I]-labeled B72.3-βG-PEG and H25-βG-PEG in LS174T tumor-bearing BALB/c nu/nu mice.

Tumor localization of B72.3-βG-PEG: FIG. 17 shows that ¹²⁵I-B72.3-βG-PEG preferentially localized in LS174T xenografts. Radioactivity of tumors and tissues was determined (A) 24, (B) 48, (C) 72 and (D) 96 h after nude mice bearing 100-200 mm³ LS174T tumors were i.v. injected with 200 μg (140 μCi) ¹²⁵I-B72.3-βG-PEG (solid columns) or ¹²⁵I-H25-βG-PEG (open columns). Results represent the mean values of three mice. Significant differences between B72.3-βG-PEG and H25-βG-PEG are indicated by; *, $p \leq 0.05$; **, $p \leq 0.005$. Bars show the standard error of the mean. Maximum accumulation of $^{125}$I-B72.3-βG-PEG in LS174T xenografts (3.11±0.8% injected dose/g) was achieved within 48 h after injection. However, the tumor to blood ratio at 48 h was only 1.9. The tumor/blood ratio of B72.3-βG-PEG increased to 4.8 at 96 h but immunoenzyme in tumors decreased about 3-fold from levels achieved at 48 h. $^{125}$I-H25-βG-PEG did not specifically localize in LS174T xenografts (FIGS. 17A-D).

Figure 18:
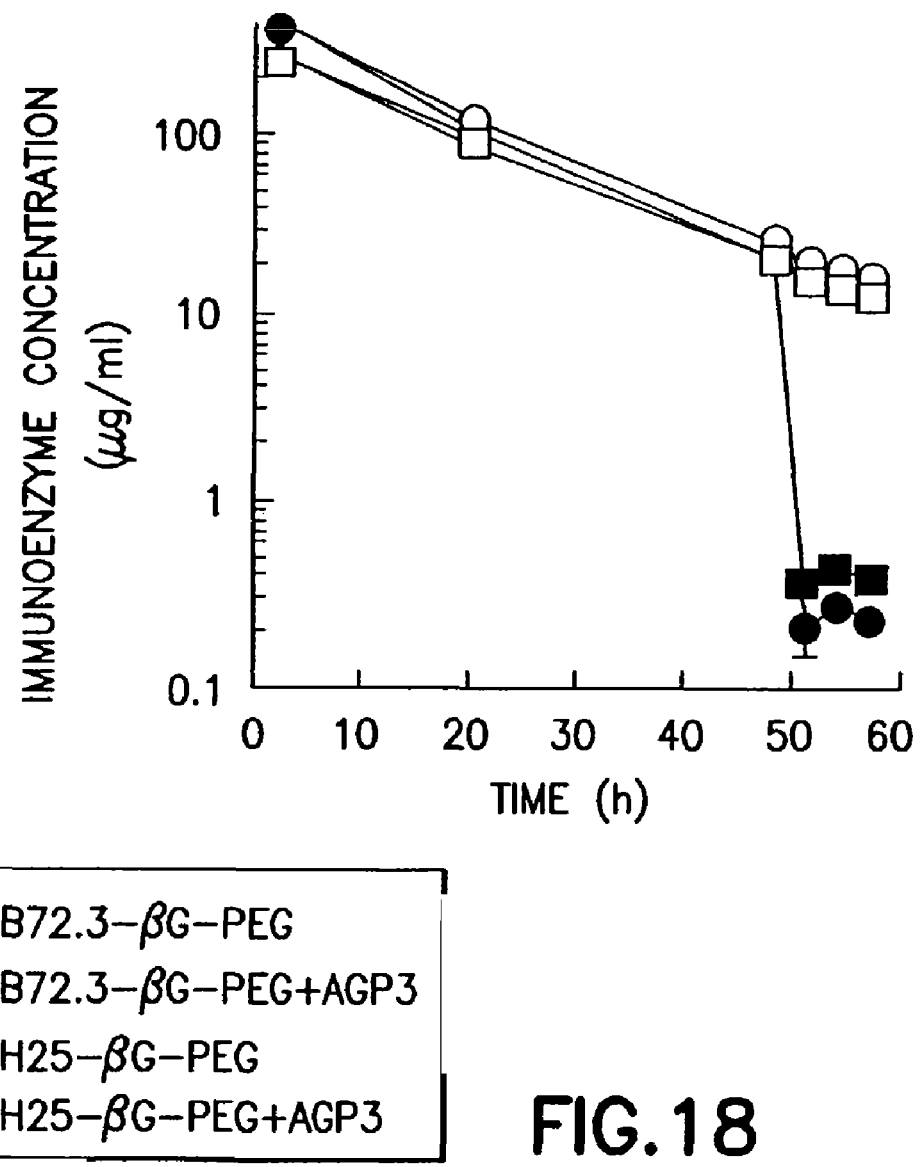
FIG. 18 shows the in vivo clearance of the PEG conjugates by the AGP3 antibody.

In vivo clearance of B72.3-βG-PEG and H25-βG-PEG: The ability of AGP3 to clear B72.3-βG-PEG and H25-βG-PEG from the circulation was examined by i.v. injecting BALB/c mice with 250 μg conjugates at time 0 followed 48 and 50 h later by two i.v. injections of 300 and 200 μg AGP3 or PBS Mean serum concentrations from 2-3 mice are shown. Bars indicate the standard error of the mean. FIG. 18 shows that AGP3 reduced the concentration of B72.3-βG-PEG in blood by 33-fold (13.4 to 0.41 μg/ml) and H25-βG-PEG by 65-fold (16.8 to 0.26 μg/ml) in 6 h.

Figure 19:
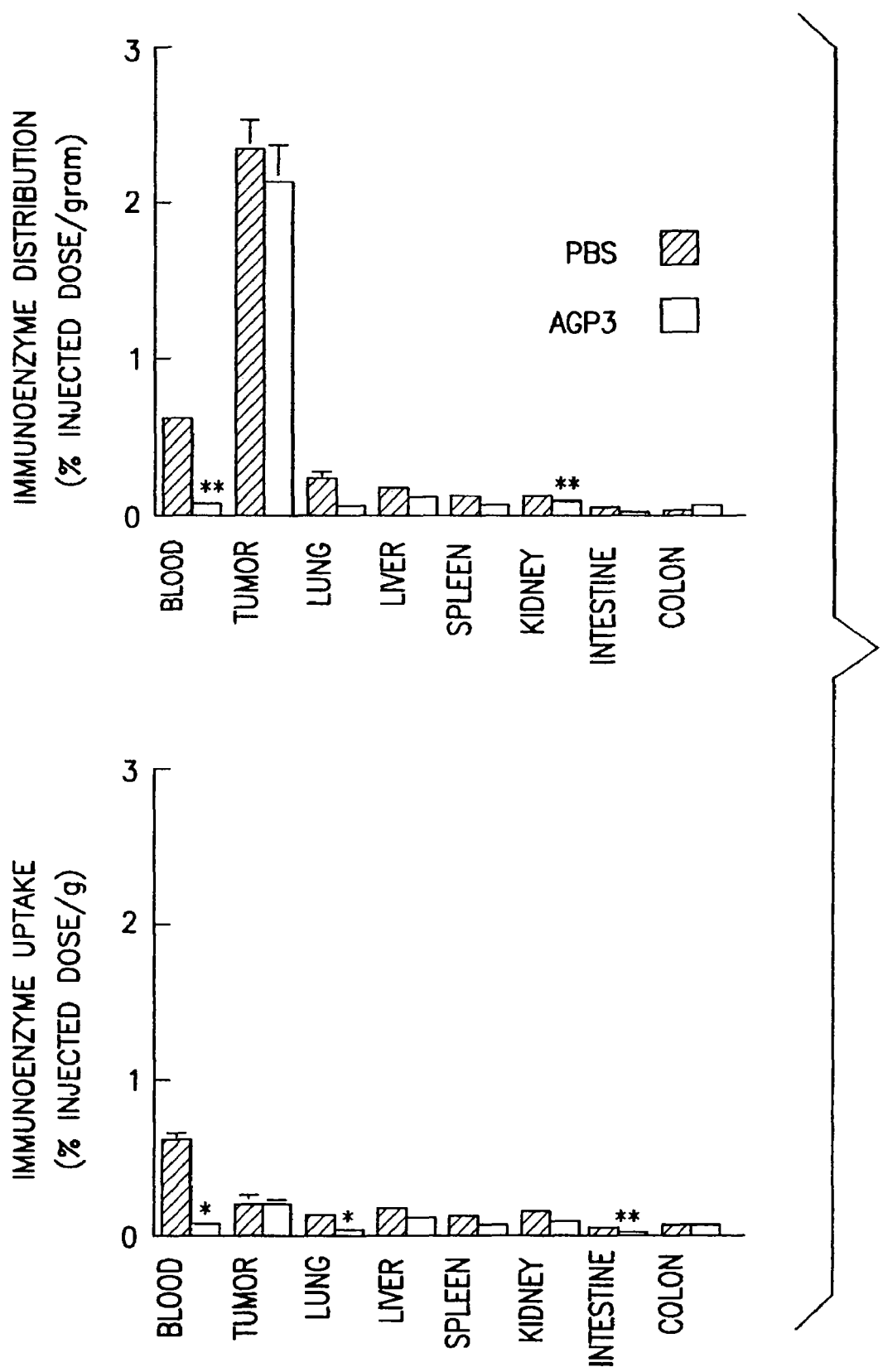
FIG. 19 shows the effect of the clearance of the PEG conjugates by the AGP3 antibody on the tumor localization.

Tumor localization of B72.3-βG-PEG with AGP3 clearance: The effect of clearance on tumor localization was determined in groups of 6-7 BALB/c nu/nu mice bearing 100-200 mm$^3$ LS174T tumor xenografts. Mice were i.v. injected at time 0 with 200 μg (140 μCi) $^{125}$I-B72.3-βG-PEG (FIG. 19A) or $^{125}$I-H25-βG-PEG (FIG. 19B). At 48 and 50 h, half the mice were i.v. injected with two fractionated doses of AGP3 (300 and 200 μg, open columns) whereas the other half received PBS (solid columns). Mice were sacrificed after 6 h and tumors, blood and organs were assayed for radioactivity. Results represent the mean values of 3-4 mice. Significant differences between immunoenzyme uptake with and without AGP3 clearance are indicated by; *, $p \leq 0.05$; **, $p \leq 0.005$. Bars show the standard error of the mean. FIG. 19A shows that tumor localization of B72.3-βG-PEG after AGP3 clearance did not significantly ($p > 0.1$) differ from tumor uptake without clearance (2.35±0.18 versus 2.14±0.23% injected dose/g). In contrast, the radioactivity in serum and all tissues except for the colon was lower with AGP3 clearance. This resulted in improved tumor/tissue ratios of B72.3-βG-PEG for most tissues (Table 3). For example, the tumor/blood ratio increased from 3.9±0.2 to 29.6±3.1. Although the control conjugate did not specifically accumulate in LS174T xenografts, clearance with AGP3 further decreased the concentration of H25-βG-PEG in the blood and most tissues (FIG. 19B). Thus, AGP3 not only reduced the serum concentration of conjugates by 33-65-fold in 6 h but also accelerated the clearance of immunoenzyme from most normal tissues. Importantly, AGP3 did not significantly reduce tumor accumulation of B72.3-βG-PEG, in contrast to some other clearance systems (Pedley et al., 1989; Sharkey et al., 1992; Kerr et al., 1993). The large size of AGP3 (IgM) may hinder passage of the mAb into the tumor interstitial space, minimizing interactions between localized immunoconjugate and AGP3. The low tumor/blood ratio without clearance can be attributed to the loss of immunoenzyme from the tumor during the prolonged period required for immunoenzyme to reach safe levels in serum. Clearance of immunoenzyme with AGP3 can allow earlier administration of prodrug when immunoenzyme localization at tumor cells is maximal.

TABLE 3

The tumor/tissues ratio of conjugates after clearance with AGP3

| | Tumor/Tissue Ratio | | | |
|---|---|---|---|---|
| | B72.3-βG-PEG | | H25-βG-PEG | |
| Tissue | No clearance | AGP3 clearance | No clearance | AGPE clearance |
| Tumor | 1 | 1 | 1 | 1 |
| Blood | 3.9 ± 0.2 | 29.6 ± 3.1 | 0.3 ± 0.1 | 2.2 ± 0.8 |
| Lung | 12.5 ± 3.3 | 33.5 ± 3.0 | 1.4 ± 0.4 | 5.5 ± 2.1 |
| Liver | 15.9 ± 2.9 | 19.2 ± 0.8 | 1.1 ± 0.2 | 1.5 ± 0.6 |
| Spleen | 19.0 ± 2.6 | 27.7 ± 5.2 | 1.8 ± 0.5 | 3.5 ± 1.5 |
| Kidney | 18.1 ± 1.3 | 31.0 ± 2.0 | 1.4 ± 0.5 | 2.2 ± 0.2 |
| Intestine | 6.4 ± 1.7 | 165 ± 56 | 4.8 ± 1.3 | 10.1 ± 2.9 |
| Colon | 54.3 ± 7.4 | 50.2 ± 8.3 | 3.6 ± 0.5 | 3.1 ± 0.33 |
| Urine | 1.1 ± 0.1 | 0.6 ± 0.1 | 0.1 ± 0.02 | 0.03 ± 0.001 |

Groups of 3 or 4 mice bearing 100–200 mm$^3$ solid LS174T tumors were injected with radiolabeled conjugates follow 48 h later by two i.v. injections of AGP3 or PBS. After 6 h, tumors, blood, urine and normal tissues were removed and counted in a gamma counter.

The radioactivity in urine after clearance of both B72.3-βG-PEG and H25-βG-PEG with AGP3 was significantly ($p \leq 0.005$) greater than without clearance (results not shown). Autoradiographic analysis of urine samples after electrophoresis on SDS PAGE revealed the presence of low-molecular-weight $^{125}$I-labeled peptides but no intact conjugates (data not shown), indicating that AGP3 clearance resulted in the rapid metabolism of conjugates.

Figure 20:
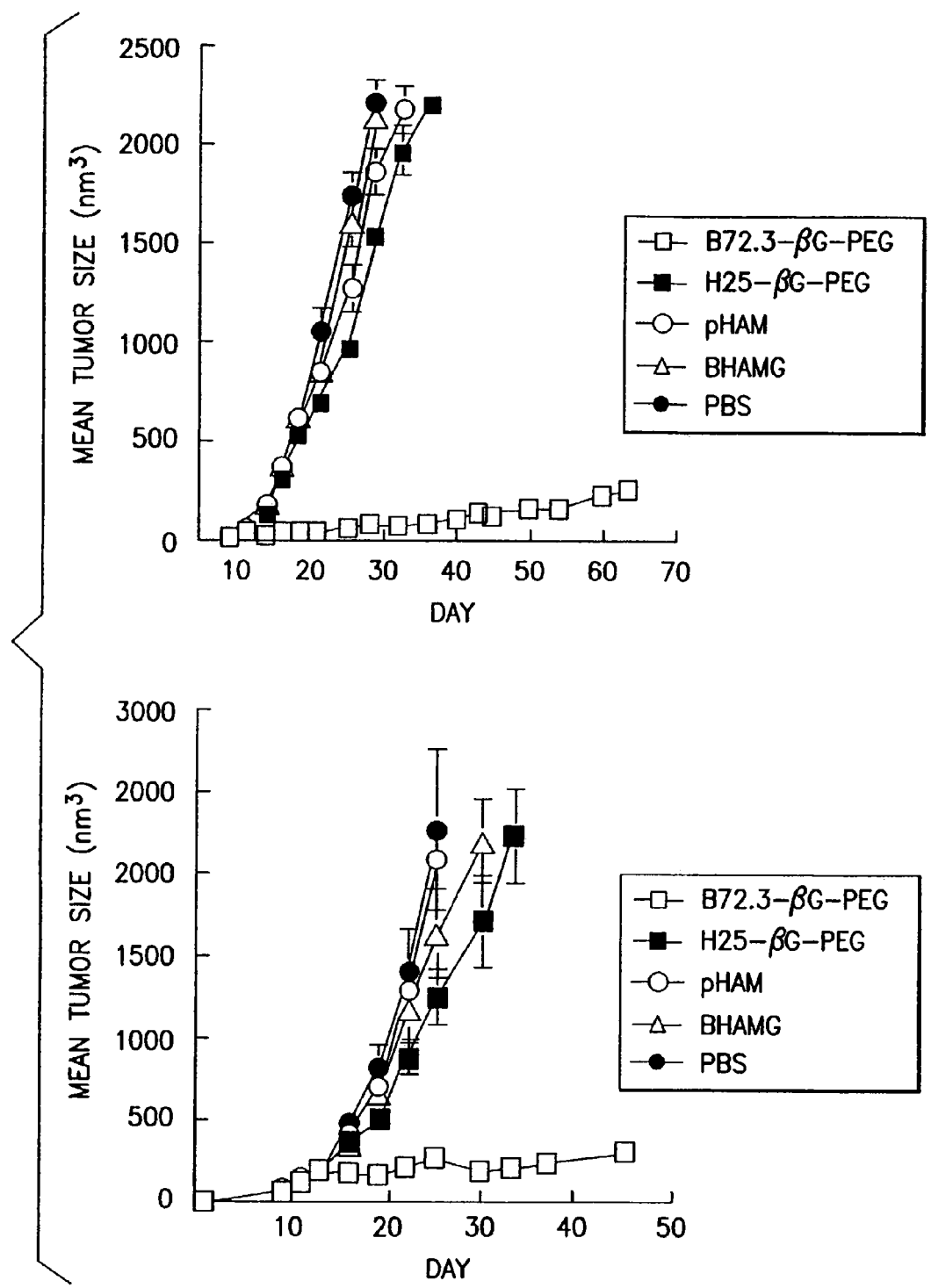
FIG. 20 shows the in vivo antitumor effect of B72.3-βG-PEG conjugate after clearance with AGP3.

Therapy of LS174T xenografts: The antitumor activity of BHAMG in combination with B72.3-βG-PEG after clearance of free conjugate with AGP3 was examined. As shown in FIG. 20A, groups of 9 BALB/c nu/nu mice bearing 50-100 mm$^3$ LS174T tumors were i.v. injected with B72.3-βG-PEG (□) or H25-βG-PEG (■) on day 9 followed by two i.v. injections of AGP3 on day 11. After 6 h, mice were i.v. injected with BHAMG (7.5 mg/kg×3). Control groups of tumor-bearing mice were treated with BHAMG (Δ), pHAM (○) or PBS (●) alone. Therapy was repeated starting on days 16, 26 and 41. Results show the mean tumor size. Bars indicate the standard error of the mean. The mean size of tumors in mice sequentially treated with B72.3-βG-PEG, AGP3 and BHAMG was significantly ($p \leq 0.0005$) smaller than control tumors after day 14. Table 4 shows that treatment toxicity with clearance was minimal with a maximum weight loss of 6% over 4 rounds of therapy. In contrast, pHAM treatment caused a maximum weight loss of 13% over 2 rounds of therapy even though it did not provide antitumor activity. As shown in FIG. 20B, groups of 8 nude mice bearing larger (200-250 mm$^3$) LS174T tumors were treated with two round of therapy as above starting on days 11 and 23. The mean size of tumors in mice sequentially treated with B72.3-βG-PEG, AGP3 and BHAMG was significantly ($p \leq 0.005$) smaller than control tumors after day 16. The degree of tumor suppression achieved with minimal toxicity by prodrug therapy compares favorably with conventional drugs such as 5-fluorouracil (Blumenthal et al., 1994) and doxorubicin (Meyer et al., 1995) in the LS174T xenograft model. B72.3-βG-PEG appeared to be rapidly catabolized into small peptides that were eliminated in the urine and possibly bile. Soluble IgM immune complexes are primarily removed from the circulation and catabolized by the mononuclear phagocyte system in the liver, spleen and lungs by receptor-mediated binding of high mannose oligosaccharides exposed upon conformational changes in IgM induced by antigen binding (Day et al., 1980). The low toxicity of BHAMG treatment observed after clearance of B72.3-βG-PEG with AGP3 indicates that cleared conjugate was unavailable for prodrug activation, consistent with rapid degradation of the immunoenzyme after clearance.

TABLE 4

Toxicity of therapy

| | Weight loss % Round of therapy | | | |
|---|---|---|---|---|
| | 1 | 2 | 3 | 4 |
| PBS | 0 | 0 | 0 | NM |
| pHAM | 6.8 | 13.0 | NM | NM |
| BHAMG | 1.7 | 4.0 | 1.7 | — |
| B72.3-BG-PEG/ AGP3/BHAMG | 35 | 5.0 | 3.8 | 6.0 |
| H25-βG-PEG/ AGP3/BHAMG | 39 | 6.6 | 4.6 | NM |

NM: not meaningful due to mouse deaths.

Most of the enzymes currently under investigation for the targeted activation of anti-neoplastic prodrugs are of microbial origin such as β-lactamase from *Enterobacter cloacae* (Kerr et al., 1995), carboxypeptidase G2 from *Pseudomonas* species (Blakey et al., 1996), β-glucuronidase (Chen et al., 1997), nitroreductase (Anlezark et al., 1995) and penicillin-G amidase (Vrudhula et al., 1993) from *Escherichia coli*, and cytosine deaminase from bakers *yeast* (Wallace et al., 1994). These enzymes are expected to induce a strong immune response as has been found for carboxypeptidase G2 in a pilot clinical trial (Sharma et al, 1996), thereby limiting the number of times that immunoenzymes can be administered to patients. The utilization of human enzymes to activate antineoplastic prodrugs may not completely prevent this problem since recombinant human proteins can also induce immune responses in patients (Atkins et al., 1986; Gribben et al., 1990). Immunosuppressive drugs such as cyclosporin A, cyclophosphamide and deoxyspergualin can decrease or delay the immune response against antibodies (ledermann et al., 1988), immunotoxins (Pai et al., 1990) and antibody-enzyme conjugates (Sharma et al., 1996). Immunosupression, in addition to producing toxicity in some patients (Sharma et al., 1996), may hinder the development of antitumor immunity generated by prodrug therapy (Chen et al., 1997).

Immune responses against proteins can be attenuated by attachment of PEG (Abuchowski et al., 1977). PEG, in contrast to immunosuppressive drugs, is not toxic and does not affect systemic immunity. PEG modification has been shown to reduce the immunogenicity of enzymes (Abuchowski et al., 1977b), antibodies (Kitamura et al., 1991), toxins (Wang et al., 1993) and recombinant human proteins (Katre, 1990). PEG-modification of bacterial enzymes may allow repeated administration of immunoenzymes for ADEPT without the need to employ toxic immunosuppressive drugs. PEG-modified enzymes of the proper molecular size can also preferentially accumulate in tumors and are under investigation for tumor selective prodrug activation (Bagshawe et al., 1999). AGP3 binds to the backbone of PEG independent of the linker or protein employed. AGP3 should therefore be generally applicable to the accelerated clearance of PEG-modified immunoenzymes, radioimmunoconjugates and imaging agents as well as for the analysis of PEG-modified proteins.

The following references are cited to further explain or describe the present invention, the contents of which are incorporated by reference.

(1) Abuchowski A, McCoy J R, Palczuk N C, van Es T and Davis F F (1977a) Effect of covalent attachment of polyethylene glycol on immunogenicity and circulating life of bovine liver catalase. *J-Biol-Chem* 252, 3582-3586.

(2) Abuchowski A, van Es T, Palczuk N C and Davis F F (1977b) Alteration of immunological properties of bovine serum albumin by covalent attachment of polyethylene glycol. *J-Biol-Chem* 252, 3578-3581.

(3) Anlezark G M, Melton R G, Sherwood R F, Wilson W R, Denny W A, Palmer B D, Knox R J, Friedlos F and Williams A (1995) Bioactivation of dinitrobenzamide mustards by an *E. coli* B nitroreductase. *Biochem Pharmacol.* 50, 609-618.

(4) Atkins M B, Gould J A, Allegretta M, Li J J, Dempsey R A, Rudders R A, Parkinson D R, Reichlin S and Mier J W (1986) Phase I evaluation of recombinant interleukin-2 in patients with advanced malignant disease. *J-Clin-Oncol* 4, 1380-1391.

(5) Bagshawe K D, Sharma S K, Know R and Amooquaye E (1999) Studies with ploymer enzyme conjugates and AMIRACS. *Advances in the Application of Monoclonal Antibodies in Clinical Oncology* Samos, Greece.

(6) Bagshawe K D, Springer C J, Searle F, Antoniw P, Sharma S K, Melton R G and Sherwood R F (1988) A cytotoxic agent can be generated selectively at cancer sites. *Br J Cancer* 58, 700-703.

(7) Basser R L, Rasko J E, Clarke K, Cebon J, Green M D, Hussein S, Alt C, Menchaca D, Tomita D, Marty J, Fox R M and Begley C G (1996) Thrombopoietic effects of pegylated recombinant human megakaryocyte growth and development factor (PEG-rHuMGDF) in patients with advanced cancer. *Lancet* 348, 1279-1281.

(8) Beatty J D, Beatty B G and Vlahos W G (1987) Measurement of monoclonal antibody affinity by non-competitive enzyme immunoassay. *J Immunol Methods* 100, 173-179.

(9) Beckman J S, Minor R L, Jr., White C W, Repine J E, Rosen G M and Freeman B A (1988) Superoxide dismutase and catalase conjugated to polyethylene glycol increases endothelial enzyme activity and oxidant resistance. *J-Biol-Chem* 263, 6884-6892.

(10) Begent R H, Ledermann J A, Green A J, Bagshawe K D, Riggs S J, Searle F, Keep P A, Adam T, Dale R G and Glaser M G (1989) Antibody distribution and dosimetry in patients receiving radiolabelled antibody therapy for colorectal cancer. *Br J Cancer* 60, 406-412.

(11) Blakey D C, Burke P J, Davies D H, Dowell R I, East S J, Eckersley K P, Fitton J E, McDaid J, Melton R G, Niculescu Duvaz I A, Pinder P E, Sharma S K, Wright A F and Springer C J (1996) ZD2767, an improved system for antibody-directed enzyme prodrug therapy that results in tumor regressions in colorectal tumor xenografts. *Cancer Res* 56, 3287-3292.

(12) Blumenthal R D, Sharkey R M, Natale A M, Kashi R, Wong G and Goldenberg D M (1994) Comparison of equitoxic radioimmunotherapy and chemotherapy in the treatment of human colonic cancer xenografts. *Cancer-Res* 54, 142-151.

(13) Bosslet K, Czech J, Seemann G, Monneret C and Hoffmann D (1994) Fusion protein mediated prodrug activation (FMPA) in vivo. *Cell Biophys* 24-25, 51-63.

(14) Bradwell A R, Vaughan A, Fairweather D S and Dykes P W (1983) Improved radioimmunodetection of tumours using second antibody [letter]. *Lancet* 1, 247.

(15) Brinckerhoff L H, Kalashnikov V V, Thompson L W, Yamshchikov G V, Pierce R A, Galavotti H S, Engelhard V H and Slingluff C L, Jr. (1999) Terminal modifications inhibit proteolytic degradation of an immunogenic MART-1(27-35) peptide: implications for peptide vaccines. *Int-J-Cancer* 83, 326-334.

(16) Cabanes A, Tzemach D, Goren D, Horowitz A T and Gabizon A (1998) Comparative study of the antitumor activity of free doxorubicin and polyethylene glycol-coated liposomal doxorubicin in a mouse lymphoma model. *Clin-Cancer-Res* 4, 499-505.

(17) Caliceti P, Monfardini C, Sartore L, Schiavon O, Baccichetti F, Carlassare F and Veronese F M (1993) Preparation and properties of monomethoxy poly(ethylene glycol) doxorubicin conjugates linked by an amino acid or a peptide as spacer. *Farmaco* 48, 919-932.

(18) Chaffee S, Mary A, Stiehm E R, Girault D, Fischer A and Hershfield M S (1992) IgG antibody response to polyethylene glycol-modified adenosine deaminase in patients with adenosine deaminase deficiency. *J-Clin-Invest* 89, 1643-1651.

(19) Chapman A P, Antoniw P, Spitali M, West S, Stephens S and King D J (1999) Therapeutic antibody fragments with prolonged in vivo half-lives. *Nat-Biotechnol* 17, 780-783.

(20) Chen B M, Chan L Y, Wang S M, Wu M F, Chern J W and Roffler S R (1997) Cure of malignant ascites and generation of protective immunity by monoclonal antibody-targeted activation of a glucuronide prodrug in rats. *Int J Cancer* 73, 392402.

(21) Chen R H, Abuchowski A, Van Es T, Palczuk N C and Davis F F (1981) Properties of two urate oxidases modified by the covalent attachment of poly(ethylene glycol). *Biochim-Biophys-Acta* 660, 293-298.

(22) Cheng T L, Chen B M, Chan L Y, Wu P Y, Chern J W and Roffler S R (1997) Poly(ethylene glycol) modification of beta-glucuronidase-antibody conjugates for solid-tumor therapy by targeted activation of glucuronide prodrugs. *Cancer-Immunol-Immunother* 44, 305-315.

(23) Cheng T L, Chen B M, Chern J W, Wu M F and Roffler S R (In press) Efficient clearance of poly(ethylene glycol)-modified immunoenzyme with anti-PEG monoclonal antibody for prodrug cancer therapy. *Bioconj Chem,*.

(24) Cheng T L, Wu P Y, Wu M F, Chern J W and Roffler S R (1999) Accelerated clearance of polyethylene glycol-modified proteins by anti-polyethylene glycol IgM. *Bioconjug-Chem* 10, 520-528.

(25) Childs C E (1975) The determination of polyethylene glycol in gamma globulin solutions. *Microchem-J* 20, 190-192.

(26) Chinol M, Casalini P, Maggiolo M, Canevari S, Omodeo E S, Caliceti P, Veronese F M, Cremonesi M, Chiolerio F, Nardone E, Siccardi A G and Paganelli G (1998) Biochemical modifications of avidin improve pharmacokinetics and biodistribution, and reduce immunogenicity. *Br-J-Cancer* 78, 189-197.

(27) Conover C D, Pendri A, Lee C, Gilbert C W, Shum K L and Greenwald R B (1997) Camptothecin delivery systems: the antitumor activity of a camptothecin-20-0-polyethylene glycol ester transport form. *Anticancer-Res* 17, 3361-3368.

(28) Day J F, Thornburg R W, Thorpe S R and Baynes J W (1980) Carbohydrate-mediated clearance of antibody antigen complexes from the circulation. The role of high mannose oligosaccharides in the hepatic uptake of IgM. antigen complexes. *J Biol Chem* 255, 2360-2365.

(29) Delgado C, Francis G E and Fisher D (1992) The uses and properties of PEG-linked proteins. *Crit Rev Ther Drug Carrier Syst* 9, 249-304:

(30) Delgado C, Pedley R B, Herraez A, Boden R, Boden J A, Keep P A, Chester K A, Fisher D, Begent R H and Francis G E (1996) Enhanced tumour specificity of an anti-carcinoembrionic antigen Fab' fragment by poly(ethylene glycol) (PEG) modification. *Br J Cancer* 73, 175-182.

(31) Divgi C R, Scott A M, Fallone P S, Hilton S, Siler K, Finn R D and Cohen A M (1994) Clinical comparison of radiolocation of two monoclonal antibodies against the TAG-72 antigen. *Nucl Med Biol* 21, 9-15.

(32) Eccles S A, Court W J, Box G A, Dean C J, Melton R G and Springer C J (1994) Regression of established breast carcinoma xenografts with antibody-directed enzyme prodrug therapy against c-erbB2 p185. *Cancer Res* 54, 5171-5177.

(33) Esslinger H U, Haas S, Maurer R, Lassmann A, Dubbers K and Muller Peltzer H (1997) Pharmacodynamic and safety results of PEG-Hirudin in healthy volunteers. *Thromb-Haemost* 77, 911-919.

(34) Fareed J, Callas D, Hoppensteadt D A, Walenga J M and Bick R L (1998) Antithrombin agents as anticoagulants and antithrombotics. Implications in drug development. *Med-Clin-North-Am* 82, 569-586.

(35) Goffin V, Bernichtein S, Carriere O. Bennett W F, Kopchick J J and Kelly P A (1999) The human growth hormone antagonist B2036 does not interact with the prolactin receptor. *Endocrinology* 140, 3853-3856.

(36) Greenwald R B, Pendri A, Conover C D, Lee C, Choe Y H, Gilbert C, Martinez A, Xia J, Wu D and Hsue M (1998) Camptothecin-20-PEG ester transport forms: the effect of spacer groups on antitumor activity. *Bioorg-Med-Chem* 6, 551-562.

(37) Gribben J G, Devereux S, Thomas N S, Keim M, Jones H M, Goldstone A H and Linch D C (1990) Development of antibodies to unprotected glycosylation sites on recombinant human GM-CSF [see comments]. *Lancet* 335, 434-437.

(38) Guermant C, Brygier J, Baeyens Volant D, Nijs M, Vincentelli J, Paul C and Looze Y (1995) Quantitative determination of polyethylene glycol based upon its salting out and partitioning of a dye into the resulting aqueous two-phase system. *Anal-Biochem* 230, 254-258.

(39) Habeeb A F (1966) Determination of free amino groups in proteins by trinitrobenzenesulfonic acid. *Anal Biochem* 14, 328-336.

(40) Haisma H J, Van Muijen M, Scheffer G, Scheper R J, Pinedo H M and Boven E (1995) A monoclonal antibody against human beta-glucuronidase for application in antibody-directed enzyme prodrug therapy. *Hybridoma* 14, 377-382.

(41) Harker L A (1999) Physiology and clinical applications of platelet growth factors. *Curr-Opin-Hematol* 6, 127-134.

(42) He X H, Shaw P C and Tam S C (1999) Reducing the immunogenicity and improving the in vivo activity of trichosanthin by site-directed pegylation. *Life Sci* 65, 355-368.

(43) Hudson P J (1998) Recombinant antibody fragments. *Curr-Opin-Biotechnol* 9, 395-402.

(44) Ito H O, So T, Hirata M, Koga T, Ueda T and Imoto T (1998) Tolerogenic activity of polyethylene glycol-conjugated lysozyme distinct from that of the native counterpart. *Immunology* 93, 200-207.

(45) Ito H O, So T, Ueda T, Imoto T and Koga T (1997) Prevention of collagen-induced arthritis (CIA) by treatment with polyethylene glycol-conjugated type II collagen; distinct tolerogenic property of the conjugated collagen from the native one. *Clin-Exp-Immunol* 108, 213-219.

(46) Johnson V G, Schlom J, Paterson A J, Bennett J, Magnani J L and Colcher D (1986) Analysis of a human tumor-associated glycoprotein (TAG-72) identified by monoclonal antibody B72.3. *Cancer Res* 46, 850-857.

(47) Kaneda Y, Yamamoto S, Kihira T, Tsutsumi Y, Nakagawa S, Miyake M, Kawasaki K and Mayumi T (1995) Synthetic cell-adhesive laminin peptide YIGSR conjugated with polyethylene glycol has improved antimetastatic activity due to a longer half-life in blood. *Invasion Metastasis* 15, 156-162.

(48) Katre N V (1990) Immunogenicity of recombinant IL-2 modified by covalent attachment of polyethylene glycol. *J-Immunol* 144, 209-213.

(49) Katre N V, Knauf M J and Laird W J (1987) Chemical modification of recombinant interleukin 2 by polyethylene glycol increases its potency in the murine Meth A sarcoma model. *Proc-Natl-Acad-Sci-U-S-A* 84, 1487-1491.

(50) Kerr D E, Garrigues U S, Wallace P M, Hellstrom K E, Hellstrom I and Senter P D (1993) Application of monoclonal antibodies against cytosine deaminase for the in vivo clearance of a cytosine deaminase immunoconjugate. *Bioconjug Chem* 4, 353-357.

(51) Kerr D E, Schreiber G J, Vrudhula V M, Svensson H P, Hellstrom I, Hellstrom K E and Senter P D (1995) Regressions and cures of melanoma xenografts following treatment with monoclonal antibody beta-lactamase conjugates in combination with anticancer prodrugs. *Cancer Res* 55, 3558-3563.

(52) Kinahan I M and Smyth M R (1991) High-performance liquid chromatographic determination of PEG 600 in human urine. *J-Chromatogr* 565, 297-307.

(53) King D J, Turner A, Farnsworth A P, Adair J R, Owens R J, Pedley R B, Baldock D, Proudfoot K A, Lawson A D, Beeley N R and et al. (1994) Improved tumor targeting with chemically cross-linked recombinant antibody fragments. *Cancer Res* 54, 6176-6185.

(54) Kirpotin D, Park J W, Hong K, Zalipsky S, Li W L, Carter P, Benz C C and Papahadjopoulos D (1997) Sterically stabilized anti-HER2 immunoliposomes: design and targeting to human breast cancer cells in vitro. *Biochemistry* 36, 66-75.

(55) Kitamura K, Takahashi T, Yamaguchi T, Noguchi A, Noguchi A, Takashina K, Tsurumi H, Inagake M, Toyokuni T and Hakomori S (1991) Chemical engineering of the monoclonal antibody A7 by polyethylene glycol for targeting cancer chemotherapy. *Cancer Res* 51, 4310-4315.

(56) Klibanov A L, Martynov A V, Slinkin M A, Sakharov I, Smirnov M D, Muzykantov V R, Danilov S M and Torchilin V P (1988) Blood clearance of radiolabeled antibody: enhancement by lactosamination and treatment with biotin-avidin or anti-mouse IgG antibodies. *J Nucl Med* 29, 1951-1956.

(57) Kobayashi H, Sakahara H, Endo K, Yao Z S, Toyama S and Konishi J (1995) Repeating the avidin "chase" markedly improved the biodistribution of radiolabelled biotinylated antibodies and promoted the excretion of additional background radioactivity. *Eur J Cancer* 31a, 1689-1696.

(58) Ledermann J A, Begent R H, Bagsbawe K D, Riggs S J, Searle F, Glaser M G, Green A J and Dale R G (1988) Repeated antitumour antibody therapy in man with suppression of the host response by cyclosporin A. *Br J Cancer* 58, 654-657.

(59) Lee W Y, Sehon A H and Akerblom E (1981) Suppression of reaginic antibodies with modified allergens. IV. Induction of suppressor T cells by conjugates of polyethylene glycol (PEG) and monomethoxy PEG with ovalbumin. *Int Arch Allergy Appl Immunol* 64, 100-114.

(60) Lee Y C, Townsend R R, Hardy M R, Lonngren J, Arnarp J, Haraldsson M and Lonn H (1983) Binding of synthetic oligosaccbarides to the hepatic Gal/GalNAc lectin. Dependence on fine structural features. *J Biol Chem* 258, 199-202.

(61) Lin L (1998) Betaseron. *Dev Biol Stand* 96, 97-104.

(62) Lodish H F (1991) Recognition of complex oligosaccharides by the multi-subunit asialoglycoprotein receptor. *Trends Biochem Sci* 16, 374-377.

(63) Maiti P K, Lang G M and Sehon A H (1988) Tolerogenic conjugates of xenogeneic monoclonal antibodies with monomethoxypolyethylene glycol. I. Induction of long-lasting tolerance to xenogeneic monoclonal antibodies. *Int J Cancer Suppl* 3, 17-22.

(64) Maloney D G, Kaminski M S, Burowski D, Haimovich J and Levy R (1985) Monoclonal anti-idiotype antibodies against the murine B cell lymphoma 38C13: characterization and use as probes for the biology of the tumor in vivo and in vitro. *Hybridoma* 4, 191-209.

(65) Marshall D, Pedley R B, Melton R G, Boden J A, Boden R and Begent R H (1995) Galactosylated streptavidin for improved clearance of biotinylated intact and F(ab')2 fragments of an anti-tumour antibody. *Br J Cancer* 71, 18-24.

(66) Martin J, Stribbling S M, Poon G K, Begent R H, Napier M, Sharma S K and Springer C J (1997) Antibody-directed enzyme prodrug therapy: pharmacokinetics and plasma levels of prodrug and drug in a phase I clinical trial. *Cancer Chemother Pharmacol* 40, 189-201.

(67) Menzel T, Schomburg A, Korfer A, Hadam M, Meffert M, Dallmann I, Casper S, Kirchner H, Poliwoda H and Atzpodien J (1993) Clinical and preclinical evaluation of recombinant PEG-IL-2 in human. *Cancer-Biother* 8, 199-212.

(68) Meyer D L, Law K L, Payne J K, Mikolajczyk S D, Zarrinmayeh H, Jungheim L N, Kling J K, Shepherd T A and Starling J J (1995) Site-specific prodrug activation by antibody-beta-lactamase conjugates: preclinical investigation of the efficacy and toxicity of doxorubicin delivered by antibody directed catalysis. *Bioconjug Chem* 6, 440-446.

(69) Meyer O, Kirpotin D, Hong K, Sternberg B, Park J W, Woodle M C and Papahadjopoulos D (1998) Cationic liposomes coated with polyethylene glycol as carriers for oligonucleotides. *J-Biol-Chem* 273, 15621-15627.

(70) Milenic D E, Esteban J M and Colcher D (1989) Comparison of methods for the generation of immunoreactive fragments of a monoclonal antibody (B72.3) reactive with human carcinomas. *J Immunol Methods* 120, 71-83.

(71) Miles P J, Langley K V, Stacey C J and Talarico T L (1997) Detection of residual polyethylene glycol derivatives in pyridoxylated-hemoglobin-polyoxyethylene conjugate. *Artif-Cells-Blood-Substit-Immobil-Biotechnol* 25, 315-326.

(72) Mullin J M, Marano C W, Laughlin K V, Nuciglio M, Stevenson B R and Soler P (1997) Different size limitations for increased transepithelial paracellular solute flux across phorbol ester and tumor necrosis factor-treated epithelial cell sheets. *J-Cell-Physiol* 171, 226-233.

(73) Nag A, Mitra G and Ghosh P C (1996) A calorimetric assay for estimation of polyethylene glycol and polyethylene glycolated protein using ammonium ferrothiocyanate. *Anal-Biochem* 237, 224-231.

(74) Nag A, Mitra G and Ghosh P C (1997) A calorimetric estimation of polyethyleneglycol-conjugated phospholipid in stealth liposomes. *Anal-Biochem* 250, 3543.

(75) Nemunaitis J (1997) A comparative review of colony-stimulating factors. *Drugs* 54, 709-729.

(76) Nishikawa M, Miyazaki C, Yamashita F, Takakura Y and Hashida M (1995) Galactosylated proteins are recognized by the liver according to the surface density of galactose moieties. *Am J Physiol* 268, G849-856.

(77) Ong G L, Ettenson D, Sharkey R M, Marks A, Baumal R, Goldenberg D M and Mattes M J (1991) Galactose-conjugated antibodies in cancer therapy: properties and principles of action. *Cancer Res* 51, 1619-1626.

(78) Paganelli G, Stella M, De Nardi P, Magnani P, Zito F, Siccardi A G, Di Carlo V and Fazio F (1991) A new method for faster blood clearance in radioimmuno-guided surgery. *J Nucl Biol Med* 35, 88-89.

(79) Pai L H, FitzGerald D J, Tepper M, Schacter B, Spitalny G and Pastan I (1990) Inhibition of antibody response to Pseudomonas exotoxin and an immunotoxin containing Pseudomonas exotoxin by 15-deoxyspergualin in mice. *Cancer-Res* 50, 7750-7753.

(80) Pedley R B, Boden J A, Boden R, Begent R H, Turner A, Haines A M and King D J (1994) The potential for enhanced tumour localisation by polyethylene glycol) modification of anti-CEA antibody. *Br J Cancer* 70, 1126-1130.

(81) Pedley R B, Dale R, Boden J A, Begent R H, Keep P A and Green A J (1989) The effect of second antibody clearance on the distribution and dosimetry of radiolabelled anti-CEA antibody in a human colonic tumor xenograft model. *Int J Cancer* 43, 713-718.

(82) Pendri A, Conover C D and Greenwald R B (1998) Antitumor activity of paclitaxel-2'-glycinate conjugated to poly(ethylene glycol): a water-soluble prodrug. *Anticancer-Drug-Des* 13, 387-395.

(83) Rice K G, Weisz O A, Barthel T, Lee R T and Lee Y C (1990) Defined geometry of binding between triantennary glycopeptide and the asialoglycoprotein receptor of rat heptocytes. *J Biol Chem* 265, 18429-18434.

(84) Richter A W and Akerblom E (1983) Antibodies against polyethylene glycol produced in animals by immunization with monomethoxy polyethylene glycol modified proteins. *Int Arch Allergy Appl Immunol* 70, 124-131.

(85) Roffler S R, Chan J and Yeh M Y (1994) Potentiation of radioimmunotherapy by inhibition of topoisomerase I. *Cancer Res* 54, 1276-1285.

(86) Roffler S R, Wang S M, Chern J W, Yeh M Y and Tung E (1991) Anti-neoplastic glucuronide prodrug treatment of human tumor cells targeted with a monoclonal antibody—enzyme conjugate. *Biochem Pharmacol* 42, 2062-2065.

(87) Rogers G T, Burke P J, Sharma S K, Koodie R and Boden J A (1995) Plasma clearance of an antibody—enzyme conjugate in ADEPT by monoclonal anti-enzyme: its effect on prodrug activation in vivo. *Br J Cancer* 72, 1357-1363.

(88) Roseng L, Tolleshaug H and Berg T (1992) Uptake, intracellular transport, and degradation of polyethylene glycol-modified asialofetuin in bepatocytes. *J-Biol-Chem* 267, 22987-22993.

(89) Ruddy S B and Hadzija B W (1994) High-performance liquid chromatographic method for the simultaneous determination of low-molecular-mass oligomers of polyethylene glycol in aqueous skin extracts. *J-Chromatogr-B-Biomed-Appl* 657, 83-92.

(90) Ryan C M, Yarmush M L and Tompkins R G (1992) Separation and quantitation of polyethylene glycols 400 and 3350 from human urine by high-performance liquid chromatography. *J-Pharm-Sci* 81, 350-352.

(91) Saito T, Nishimura H, Sekine T, Urushibara T, Kodera Y, Hiroto M, Matsushima A and Inada Y (1996) Tolerogenic capacity of poly(ethylene glycol) (PEG)—modified ovalbumins in relation to their immunoreactivity towards anti-ovalbumin antibody. *J Biomater Sci Polym Ed* 8, 311-321.

(92) Sandborn W J and Hanauer S B (1999) Antitumor necrosis factor therapy for inflammatory bowel disease: a review of agents, pharmacology, clinical results, and safety. *Inflamm-Bowel-Dis* 5, 119-133.

(93) Savoca K V, Abuchowski A, van Es T, Davis F F and Palczuk N C (1979) Preparation of a non-immunogenic arginase by the covalent attachment of polyethylene glycol. *Biochim-Biophys-Acta* 578, 47-53.

(94) Savoca K V, Davis F F and Palczuk N C (1984) Induction of tolerance in mice by uricase and monomethoxypolyethylene glycol-modified uricase. *Int Arch Allergy Appl Immunol* 75, 58-67.

(95) Senter P D, Saulnier M G, Schreiber G J, Hirschberg D L, Brown J P, Hellstrom I and Helistrom K E (1988) Anti-tumor effects of antibody-alkaline phosphatase conjugates in combination with etoposide phosphate. *Proc Natl Acad Sci USA* 85, 4842-4846.

(96) Sharkey R M, Boerman O C, Natale A, Pawlyk D, Monestier M, Losman M J and Goldenberg D M (1992) Enhanced clearance of radiolabeled murine monoclonal antibody by a syngeneic anti-idiotype antibody in tumor-bearing nude mice. *Int J Cancer* 51, 266-273.

(97) Sharkey R M, Primus F J and Goldenberg D M (1984) Second antibody clearance of radiolabeled antibody in cancer radioimmunodetection. *Proc Natl Acad Sci USA* 81, 2843-2846.

(98) Sharma S K, Bagsbawe K D, Burke P J, Boden J A, Rogers G T, Springer C J, Melton R G and Sherwood R F (1994) Galactosylated antibodies and antibody-enzyme conjugates in antibody-directed enzyme prodrug therapy. *Cancer* 73, 1114-1120.

(99) Sharma S K, Bagshawe K D, Burke P J, Boden R W and Rogers G T (1990) Inactivation and clearance of an anti-CEA carboxypeptidase G2 conjugate in blood after localisation in a xenograft model. *Br J Cancer* 61, 659-662.

(100) Sharma S K, Bagshawe K D, Melton R G and Begent R H (1996) Effect of cyclosporine on immunogenicity of a bacterial enzyme carboxypeptidase G2 in ADEPT. *Transplant Proc* 28, 3154-3155.

(101) Stella M, De Nardi P, Paganelli G, Magnani P, Mangili F, Sassi I, Baratti D, Gini P, Zito F, Cristallo M and et al. (1994) Avidin-biotin system in radioimmunoguided surgery for colorectal cancer. Advantages and limits. *Dis Colon Rectum* 37, 335-343.

(102) Stewart J S, Sivolapenko G B, Hird V, Davies K A, Walport M, Ritter M A and Epenetos A A (1990) Clearance of 131I-labeled murine monoclonal antibody from patients' blood by intravenous human anti-murine immunoglobulin antibody. *Cancer Res* 50, 563-567.
(103) Stocks S J, Jones A J, Ramey C W and Brooks D E (1986) A fluorometric assay of the degree of modification of protein primary amines with polyethylene glycol. *Anal Biochem* 154, 232-234.
(104) Suzuki T, Kanbara N, Tomono T, Hayashi N and Shinohara I (1984) Physicochemical and biological properties of poly(ethylene glycol)-coupled immunoglobulin G. *Biochim-Biophys-Acta* 788, 248-255.
(105) Svensson H P, Frank I S, Berry K K and Senter P D (1998). Therapeutic effects of monoclonal antibody-beta-lactamase conjugates in combination with a nitrogen mustard anticancer prodrug in models of human renal cell carcinoma. *J Med Chem* 41, 1507-1512.
(106) Tennvall J, Garkavij M, Chen J, Sjogren H O and Strand S E (1997) Improving tumor-to-normal-tissue ratios of antibodies by extracorporeal immunoadsorption based on the avidin-biotin concept: development of a new treatment strategy applied to monoclonal antibodies murine L6 and chimeric BR96. *Cancer* 80, 2411-2418.
(107) Thor A, Obuchi N, Szpak C A, Johnston W W and Scblom J (1986) Distribution of oncofetal antigen tumor-associated glycoprotein-72 defined by monoclonal antibody B72.3. *Cancer Res* 46, 3118-3124.
(108) Thornburg R W, Day J F, Baynes J W and Thorpe S R (1980) Carbohydrate-mediated clearance of immune complexes from the circulation A role for galactose residues in the hepatic uptake of IgG-antigen complexes. *J Biol Chem* 255, 6820-6825.
(109) Townsend R R, Hardy M R, Wong T C and Lee Y C (1986) Binding of N-linked bovine fetuin glycopeptides to isolated rabbit hepatocytes: Gal/GalNAc hepatic lectin discrimination between Gal beta(1,4)GlcNAc and Gal beta(1,3)GlcNAc in a triantennary structure. *Biochemistry* 25, 5716-5725.
(110) Ullen A, Riklund Ahlstrom K, Makiya R and Stigbrand T (1995,a) Syngeneic anti-idiotypic antibodies eliminate excess radiolabeled idiotypes at experimental radioimmunolocalization. *Cell Biophys* 27, 3145.
(111) Ullen A, Sandstrom P, Ahlstrom K R, Sundstrom B, Nilsson B, Arlestig L and Stigbrand T (1995b) Use of anticytokeratin monoclonal anti-idiotypic antibodies to improve tumor:nontumor ratio in experimental radioimmunolocalization. *Cancer Res* 55, 5868s-5873s.
(112) Vrudhula V M, Senter P D, Fischer K J and Wallace P M (1993) Prodrugs of doxorubicin and melphalan and their activation by a monoclonal antibody-penicillin-G amidase conjugate. *J Med Chem* 36, 919-923.
(113) Wallace P M, MacMaster J F, Smith V F, Kerr D E, Senter P D and Cosand W L (1994) Intratumoral generation of 5-fluorouracil mediated by an antibody-cytosine deaminase conjugate in combination with 5-fluorocytosine. *Cancer Res* 54, 2719-2723.
(114) Wang Q C, Pai L H, Debinski W, FitzGerald D J and Pastan I (1993) Polyethylene glycol-modified chimeric toxin composed of transforming growth factor alpha and Pseudomonas exotoxin. *Cancer-Res* 53, 4588-4594.
(115) Wang S M, Chern J W, Yeh M Y, Ng J C, Tung E and Roffler S R (1992) Specific activation of glucuronide prodrugs by antibody-targeted enzyme conjugates for cancer therapy. *Cancer Res* 52, 4484-4491.
(116) Yabe Y, Nishikawa M, Tamada A, Takakura Y and Hashida M (1999) Targeted delivery and improved therapeutic potential of catalase by chemical modification: combination with superoxide dismutase derivatives. *J-Pharmacol-Exp-Ther* 289, 1176-1184.
(117) Yeh M Y, Hellstrom I, Brown J P, Warner G A, Hansen J A and Hellstrom K E (1979) Cell surface antigens of human melanoma identified by monoclonal antibody. *Proc Natl Acad Sci USA* 76, 2927-2931.

The invention is not limited by the embodiments described above which are presented as examples only but can be modified in various ways within the scope of protection defined by the appended patent claims.

We claim:

1. A method of accelerating the clearance of a polyethylene glycol-containing compound from the circulating blood of a patient to whom the polyethylene glycol-containing compound was previously administered, comprising the step of administering to the patient a pharmaceutical composition comprising an anti-polyethylene glycol monoclonal antibody, wherein the antibody is obtained via immunizing a mouse with an RH1-βG-PEG conjugate, and the polyethylene glycol-containing compound comprises B72.3-βG-PEG or H25-βG-PEG.

2. The method of claim 1, wherein the anti-polyethylene glycol antibody is administered to the patient less than 10 days after administering the polyethylene glycol-containing compound to the patient.

3. The method of claim 1, wherein the anti-polyethylene glycol antibody is administered to the patient less than 5 days after administering the polyethylene glycol-containing compound to the patient.

4. The method of claim 1, wherein the anti-polyethylene glycol antibody is administered to the patient from 24 hours to 5 days after administering the polyethylene glycol-containing compound to the patient.

5. The method of claim 1, wherein the monoclonal antibody is an IgM antibody.

6. The method of claim 1, wherein the anti-polyethylene glycol antibody is conjugated to galactose so as to be targeted by an asialoglycoprotein receptor on a hepatocyte and uptaken by the hepatocyte.

7. A method of treating a patient suffering from a TAG-72$^+$tumor, comprising the steps of:
a) administering to the patient a polyethylene glycol-containing compound comprising B72.3-βG-PEG;
b) administering to the patient after step (a) an anti-polyethylene glycol monoclonal antibody obtained via immunizing a mouse with an RH1-βG-PEG conjugate to accelerate the clearance of the polyethylene glycol-containing compound from the patient's circulating blood; and
c) administering to the patient after step (b) a β-glucouronidase-activatable anti-tumor prodrug.

8. The method of claim 7, wherein the anti-polyethylene glycol antibody is administered to the patient less than 10 days after administering the polyethylene glycol-containing conjugate to the patient.

9. The method of claim 7, wherein the anti-polyethylene glycol antibody is administered to the patient less than 5 days after administering the polyethylene glycol-containing conjugate to the patient.

10. The method of claim 7, wherein the anti-polyethylene glycol antibody is administered to the patient from 24 hours to 5 days after administering the polyethylene glycol-containing conjugate to the patient.

11. The method of claim 7, wherein the monoclonal antibody is an IgM antibody.

12. The method of claim 7, wherein the anti-polyethylene glycol antibody is conjugated to galactose so as to be targeted by an asialoglycoprotein receptor on a hepatocyte and uptaken by the hepatocyte.

13. The method of claim 7, wherein the anti-tumor prodrug is a tetra n-butyl ammonium salt of a glucuronide derivative of p-hydroxyaniline mustard.

14. The method of claim 1, wherein the anti-polyethylene glycol monoclonal antibody is produced by the hybridoma having CCTCC deposit number CCTCC-V-200001.

15. The method of claim 7, wherein the anti-polyethylene glycol monoclonal antibody is produced by the hybridoma having CCTCC deposit number CCTCC-V-200001.

* * * * *